(12) United States Patent
Yamazaki et al.

(10) Patent No.: US 10,004,667 B2
(45) Date of Patent: Jun. 26, 2018

(54) ORGANIC-INORGANIC COMPOSITE FILLER, AND METHOD FOR PRODUCING THE SAME

(75) Inventors: Tatsuya Yamazaki, Tokyo (JP); Hironobu Akizumi, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 33 days.

(21) Appl. No.: 14/343,626

(22) PCT Filed: Sep. 13, 2012

(86) PCT No.: PCT/JP2012/073516
§ 371 (c)(1),
(2), (4) Date: Mar. 7, 2014

(87) PCT Pub. No.: WO2013/039169
PCT Pub. Date: Mar. 21, 2013

(65) Prior Publication Data
US 2014/0213687 A1    Jul. 31, 2014

(30) Foreign Application Priority Data

Sep. 15, 2011   (JP) ................... 2011-201396

(51) Int. Cl.
*A61K 6/00* (2006.01)
*A61K 6/083* (2006.01)
(Continued)

(52) U.S. Cl.
CPC ............ *A61K 6/0073* (2013.01); *A61K 6/083* (2013.01); *C08F 2/44* (2013.01); *C08F 292/00* (2013.01);
(Continued)

(58) Field of Classification Search
CPC ......... Y10T 428/2993; Y10T 428/2998; A61F 2013/530489; A61K 6/0073;
(Continued)

(56) References Cited

U.S. PATENT DOCUMENTS

| 6,221,931 B1 | 4/2001 | Sakuma et al. | |
| 2004/0054028 A1* | 3/2004 | Hattori | A61K 6/0023 523/118 |

(Continued)

FOREIGN PATENT DOCUMENTS

| JP | 2000-80013 A | 3/2000 |
| JP | 2008-37952 A | 2/2008 |
| WO | 2011/115007 A1 | 9/2011 |

OTHER PUBLICATIONS

Machine translation of JP 2003-012460 by Miyazaki et al. 2003.*
(Continued)

*Primary Examiner* — Randy P Gulakowski
*Assistant Examiner* — Christina H Wales
(74) *Attorney, Agent, or Firm* — Norris McLaughlin & Marcus PA

(57) ABSTRACT

An organic-inorganic composite filler contains: inorganic aggregate particles formed by aggregation of inorganic primary particles with an average particle diameter of 10 to 1000 nm; an organic resin phase including a cured polymer of a polymerizable monomer covering surfaces of the inorganic primary particles and bonding the inorganic primary particles to each other, and a water absorbing resin; and aggregation gaps with a volume of micropores formed between parts of the organic resin phase of 0.01 to 0.30 $cm^3/g$ in pore volume measurement within a pore diameter range of 1 to 500 nm, as measured by a mercury intrusion technique. In a cross section passing through the centers of the inorganic aggregate particles, based on 100 measured (Continued)

inorganic particles, there are 10 or less inorganic aggregate particles having a macro void with a maximum width of at least 1 μm.

13 Claims, 2 Drawing Sheets

(51) Int. Cl.
  *C08F 2/44* (2006.01)
  *C08F 292/00* (2006.01)
  *C08K 9/04* (2006.01)
  *C08K 3/013* (2018.01)
  *C08K 9/08* (2006.01)
(52) U.S. Cl.
  CPC ............... *C08K 3/013* (2018.01); *C08K 9/04* (2013.01); *C08K 9/08* (2013.01)
(58) Field of Classification Search
  CPC .. A61K 6/0008; A61K 6/0088; A61K 6/0612; A61K 6/0681; A61K 6/08
  See application file for complete search history.

(56) References Cited

U.S. PATENT DOCUMENTS

2007/0184185 A1* 8/2007 Besinger .............. A61K 6/0073
  427/212
2011/0257292 A1* 10/2011 Okubayashi ......... A61K 6/0005
  523/115
2013/0005846 A1* 1/2013 Yamazaki ............ A61K 6/0073
  521/149

OTHER PUBLICATIONS

Machine translation of JP 06-135813 by Hattori et al. 1994.*
Daniela Lubasova,ab Haitao Niu,b Xueting Zhaob and Tong Lin. Hydrogel properties of electrospun polyvinylpyrrolidone and polyvinylpyrrolidone/poly(acrylic acid) blend nanofibers. RSC Advances 2015, 5, 54481-54487.*
International Search Report dated Oct. 9, 2012.
English Translation of International Search Report dated Oct. 9, 2012.

* cited by examiner

ORGANIC-INORGANIC COMPOSITE FILLER, AND METHOD FOR PRODUCING THE SAME

This application is a 371 application of PCT/JP2012/073516 filed Sep. 13, 2012, which claims foreign priority benefit under 35 U.S.C. § 119 of Japanese application Nos. 2011-201396 filed Sep. 15, 2011, the disclosure of each of which is incorporated by reference herein in their entirety.

TECHNICAL FIELD

The present invention relates to an organic-inorganic composite filler, a producing method therefor, and a dental curable composition containing the organic-inorganic composite filler.

BACKGROUND ART

A dental composite restorative material is a typical dental curable composition. In a dental clinic, for example, the dental composite restorative material is filled into a cavity of a tooth to be restored, and then formed into the tooth shape. Subsequently, the formed dental composite restorative material is polymerized and cured by irradiation with active light with the use of a special irradiator. In this manner, the damaged tooth is restored.

In a dental laboratory, the dental composite restorative material is built-up in the shape of a tooth to be restored on a plaster cast, and then polymerized and cured by irradiation with light. The resulting prosthesis is, in a dental clinic, bonded to the tooth with a dental adhesive. In this manner, the damaged tooth is restored.

A dental composite restorative material is advantageous in that, this can provide substantially the same color as that of a natural tooth, and has good handling property. In recent years, therefore, the dental composite restorative material has spread rapidly, and now is applied in most of the treatments for anterior teeth. Furthermore, a dental composite restorative material has also been developed which provides the cured product thereof with considerably high mechanical strength. As a result, the dental composite restorative material is beginning to be applied also in the restoration of a posterior tooth, to which high bite pressure is loaded.

A dental composite restorative material generally includes a polymerizable monomer (monomer), a filler, and a polymerization initiator as main components. Furthermore, when the filler is added to the dental composite restorative material, the type, shape, particle diameter, loading amount and the like of the filler to be used are chosen. When they are chosen appropriately, various properties such as the handling property of the paste-like dental composite restorative material, and the esthetics and mechanical strength of the cured product are controlled optimally.

For example, when inorganic fillers with a large particle diameter are added to a dental composite restorative material, the resulting composite restorative material can form a cured product with high mechanical strength. Unfortunately, however, the cured product may have reduced surface smoothness or wear resistance. As a result, it is difficult to obtain a cured product with a glossy finish surface like a natural tooth.

Furthermore, adding fine inorganic fillers with an average particle diameter of 1 μm or less into a dental composite restorative material can provide a cured product with good surface smoothness or wear resistance. However, such fine inorganic fillers have a large specific surface area, thereby significantly increasing the viscosity of a paste-like composite restorative material. In the treatment of a tooth, it is necessary for a dentist to previously adjust the viscosity of a dental composite restorative material to a level suitable for use in the oral cavity. In order to reduce the viscosity, it is necessary to reduce the content of fine inorganic fillers. However, such a reduction of the content of fine inorganic fillers may result in an increase in the shrinkage of the resulting cured product, which is associated with the polymerization of a monomer during the curing of the composite restorative material, a reduction in the mechanical strength of the resulting cured product, and the like.

Under such circumstances, the use of an organic-inorganic composite filler is proposed (see for example Patent Literatures 1 and 2). According to these Patent Literatures, using such an organic-inorganic composite filler may provide a paste-like composite restorative material having good handling property, while maintaining good surface smoothness and wear resistance of the cured product as in a case where a fine inorganic filler is used, and further reduces the polymerization shrinkage of the cured product.

Such an organic-inorganic composite filler is a composite filler including an organic resin in which fine inorganic fillers are contained. The organic-inorganic composite fillers have a surface area smaller than that of the above mentioned fine inorganic fillers. Therefore, even adding a sufficient amount of the organic-inorganic composite filler can obtain a paste-like composite restorative material without causing thickening.

A general method for producing the above mentioned organic-inorganic composite filler includes previously kneading fine inorganic fillers and a polymerizable monomer to form a curable composition, polymerizing and curing the curable composition to form, a cured product, and then grinding the cured product (see paragraph [0012] of Patent Literature 1).

There is also known a method for producing an organic-inorganic composite filler with a narrow particle size distribution (see Claims of Patent Literature 2). This method includes firstly granulating fine inorganic fillers by a method such as spray drying to produce inorganic aggregate particles. Subsequently, the method includes bringing the produced inorganic-aggregate particles into contact with a liquid polymerizable monomer under reduced pressure, and then returning the reduced pressure to the normal pressure. According to this step, the polymerizable monomer is allowed to penetrate aggregation gaps among primary particles constituting the inorganic aggregate particles. Subsequently, the method includes polymerizing and curing the penetrating monomer to form an organic-inorganic composite filler. This organic-inorganic composite filler may also be used without being ground.

The Literature describes that in the producing method, the polymerizable monomer may be diluted with a volatile solvent when the inorganic aggregate particles are brought into contact with the polymerizable monomer (paragraphs [0042] to [0043]). The reason is that the polymerizable monomer should be allowed to sufficiently penetrate the aggregation, gaps among the inorganic aggregate particles.

Unfortunately, the description in the specification of the Literature is silent on how the volatile solvent should be used. The description is also silent on what process should be specifically used to remove the volatile solvent after the monomer penetrates the aggregation gaps. Furthermore, the Literature discloses a dropping or continuous mixing method as a method for bringing the polymerizable monomer into contact with the inorganic aggregate particles. Such a continuous contact method is directed to allow as much the polymerizable monomer as possible to penetrate the aggregation gaps among the inorganic aggregate particles.

From the above description, therefore, it is apparent that also in an aspect of diluting the above mentioned polymerizable monomer with a volatile solvent, the technical idea is unchanged of loading the polymerizable monomer as much as possible into the aggregation gaps.

In other words, it suggests that the volatile solvent should be used in a necessary minimum amount. Therefore, it is considered that in an aspect of diluting the polymerizable monomer with a volatile solvent, the diluting solution of the polymerizable monomer is allowed to penetrate the aggregation gaps, while the volatile solvent is evaporated from the penetrating diluting solution in parallel.

Thus, it is considered chat the dilution aspect is intended to fill the whole aggregation gap with a sufficient amount of the polymerizable monomer through the continuous penetration and evaporation before the polymerization and curing.

CITATION LIST

Patent Literature

Patent Literature 1: JP 2000-80013 A
Patent Literature 2: JP 2008-37952 A

SUMMARY OF INVENTION

Technical Problem

A cured product of a dental composite restorative material added an organic-inorganic composite filler, which is obtained by the above mentioned conventional method, has considerably high mechanical strength. However, as such a material is increasingly applied to, for example, the restoration of a posterior tooth, to which high occlusal pressure is loaded as described above, there has been more demand for the improvement of the mechanical strength of an organic-inorganic composite filler. Therefore, it is desired to further increase the mechanical strength of an organic-inorganic composite filler.

Under the circumstances, the inventors previously proposed a novel organic-inorganic composite filler for providing a cured produce with higher mechanical strength, when used as a filler for a dental composite restorative material (PCT/JP 2011/55757).

This organic-inorganic composite filler is an organic-inorganic composite filler, including: inorganic aggregate particles formed by aggregation of inorganic primary particles with an average particle diameter of 10 to 1000 nm; an organic resin phase with which a surface of each inorganic primary particle is covered and with which the inorganic primary particles are bonded to each other; and aggregation gaps that are formed between parts of the organic resin phase, with which the surface of each inorganic primary particle is covered, and have a pore volume of 0.01 to 0.30 cm$^3$/g as measured by a mercury intrusion technique, wherein the pore volume corresponds to a volume of pores with a pore diameter in the range of 1 to 500 nm.

In this organic-inorganic composite filler, pores (i.e., micropores) with a pore diameter in the range of 1 to 500 nm are formed having a specific volume, which pores result from the aggregation gaps among the inorganic primary particles. Thus, when this organic-inorganic composite filler is added to a dental curable composition, a polymerizable monomer penetrates by capillarity such micropores, while sufficiently filling the micropores. When the polymerizable monomer filled in this way is cured, the inside and outside of the filler are covered together with a cured resin, leading to strong adhesion of the cured resin to the filler (so-called anchoring effect). As a result, the inorganic filler is retained with high interlocking strength in a cured product. This adhesion is much stronger than adhesion between a conventional filler and a cured resin that are adhered only on a filler surface to each other.

This organic-inorganic composite filler is produced by a method including the steps of: immersing inorganic aggregate particles, which include inorganic aggregate particles formed by aggregation of inorganic primary particles with an average particle diameter of 10 to 1000 nm, in a polymer 1 sable monomer solution containing 100 parts by mass of an organic solvent, 3 to 70 parts by mass of a polymerizable monomer, and an effective amount of a polymerisation initiator; then removing the organic solvent from the inorganic aggregate particles after the immersion; and then polymerizing and curing the polymerizable monomer with which the inorganic aggregate particles are impregnated.

In this producing method, when inorganic aggregate particles, which include the above mentioned inorganic aggregate particles formed by aggregation, of inorganic primary particles with an average particle diameter of 10 to 1000 nm, are produced by a granulation procedure using the spray drying, the micropores resulting from the aggregation gaps among the inorganic primary particles may be easily formed so as to have a large volume. Therefore, using this method may easily produce an organic-inorganic composite filler having the above mentioned micropore properties.

Because the organic-inorganic composite filler produced by the above mentioned method has micropores with a specific pore volume, as described above, it is very advantageous in improvement of the mechanical strength. Unfortunately, in these inorganic aggregate particles, however, based on the observation of a cross section passing through she centers of the inorganic aggregate particles, it was found that there included quite a lot of inorganic aggregate particles forming a huge cavity (macro void) thereinside with a maximum width of at least 1 μm. Further examination revealed that the organic-inorganic composite filler obtained by the above mentioned producing method has, due to the formation of the developed macro void, a dimpled shape with a deep dimple on the surface of the particles, and a toroidal shape in which a dimple penetrates the particles. Furthermore, even when the shape was spherical or nearly spherical, the above mentioned macro void was often formed thereinside to give a hollow shape.

Because the pore diameter is large, the macro void cannot almost obtain an improvement, effect of the mechanical strength through an interlocking strength like the above mentioned micropore. Furthermore, when a dental curable composition is manufactured, because a polymerizable monomer penetrates the macro void but insufficiently fill the macro void, the macro void remains unfilled as it is in the filler. The remaining unfilled macro void has a size that is easy to hold a colored component of food or beverage. Therefore, when a cured product of the dental curable composition added the organic-inorganic composite filler in which the macro void remains is used in the oral cavity for a long term, there arises a new problem in that the discoloration resistance is inferior in some degree.

In particular, in dental treatment in which a dental composite restorative material is used, the surface of a cured, product is often polished. In this case, even when the shape of an organic-inorganic composite filler having the macro void thereinside is spherical or nearly spherical, a lot of macro voids inside the organic-inorganic composite fillers are exposed to the polished surface of the cured product, with the result that the discoloration resistance is degraded.

Under the above mentioned circumstances, an object of the present invention is to provide an organic-inorganic composite filler and a method for producing the same, and a dental curable composition containing the organic-inorganic composite filler, in which the organic-inorganic composite filler has features that generation of a macro void is prevented and micropores are formed, so that a dental curable composition, which is added the organic-inorganic composite filler and is cured, can be provided with a high mechanical strength and increased discoloration resistance.

Solution to Problem

The inventors have made earnest studies to solve the above problems. As a result, the inventors have found that a macro void in an organic-inorganic composite filler is formed when inorganic aggregate particles are produced by spray drying of inorganic primary particles that are a raw material. In a spray drying method, inorganic primary particles with an average particle diameter of 10 to 1000 nm are used to prepare an aqueous suspension. Subsequently, sprayed droplets of the suspension are brought into contact with high-temperature gas to volatilize the aqueous medium, so that the contained inorganic primary particles aggregate.

The inventors have found that in a spray drying method, the volatilization of the aqueous medium firstly occurs at the surface of the sprayed droplet in the early stage of drying, and subsequently the volatilization progresses toward the inner side of the sprayed droplet at once, so that the aggregate of the inorganic primary particles lacks uniformity, which leads to the formation of a macro void inside the resulting inorganic aggregate particles. Therefore, based on the finding, the inventors have found, that devising a better spray drying can eliminate the lack of uniformity of this aggregate and substantially reduce the macro void, and thus have accomplished the present invention.

That is, the present invention is an organic-inorganic composite filler, including: inorganic aggregate particles formed by aggregation of inorganic primary particles with an average particle diameter of 10 to 1000 nm; an organic resin phase including a cured polymer of a polymerisable monomer covering surfaces of the inorganic primary particles and bonding the inorganic primary particles to each other, and a water absorbing resin; and aggregation gaps with a volume of micropores formed between parts of the organic resin phase of 0.01 to 0.30 cm$^3$/g in pore volume measurement within a pore diameter range of 1 to 500 nm, as measured by a mercury intrusion technique, wherein in a cross section passing through centers of the inorganic aggregate particles, based on 100 measured inorganic particles, there are 10 or less inorganic aggregate particles having a macro void with a maximum width of at least 1 µm.

Further, the present invention is a method for producing the organic-inorganic composite filler including the steps of: spray drying an aqueous suspension of the inorganic primary particles with an average particle diameter of 10 to 1000 nm containing the water absorbing resin to granulate the inorganic primary particles, so that the inorganic aggregate particles are formed in which the surfaces of the inorganic primary particles are attached with the water absorbing resin; immersing the formed inorganic aggregate particles with a polymerizable monomer solution containing 100 parts by mass of an organic solvent, 3 to 70 parts by mass of the polymerizable monomer, and an effective amount of a polymerization initiator; removing the organic solvent from, the immersed inorganic aggregate particles; and polymerizing and curing the polymerizable monomer with which the inorganic aggregate particles are impregnated.

Advantageous Effects of Invention

The organic-inorganic composite filler of the present invention can impart the effects such as improvement of the paste handling property and reduction of the volume shrinkage by polymerization to a dental, curable composition added the filler. Furthermore, the organic-inorganic composite filler of the present invention can form a cured product of the composition with significantly enhanced surface smoothness and highly increased mechanical strength. These effects are obtained when micropores with a pore diameter of 1 to 500 nm are formed of aggregation gaps among inorganic primary particles so as to have a specific volume in the organic-inorganic composite filler.

In the dental curable composition, a polymerizable monomer contained in the dental curable composition penetrates by capillarity the micropores formed of the aggregation gaps in the organic-inorganic composite filler. Therefore, an anchoring effect is obtained in the cured product, so that the organic-inorganic composite filler is retained in the cured product with high interlocking strength. As a result, it is speculated that the cured product has enhanced mechanical strength.

Furthermore, the organic-inorganic composite filler of the present invention has substantially no macro void with a maximum width of at least 1 µm in a cross section passing through the center of the inorganic aggregate particles. As a result, even when the cured product of the dental curable composition added the organic-inorganic composite filler is brought into contact with a colored component of food or beverage in the oral cavity, the cured product hardly hold the colored component of food or beverage, so that good discoloration resistance is maintained.

The organic-inorganic composite filler of the present invention having such advantageous effects can be used as a filler, without any limitation, in a variety of applications such as dental materials and cosmetic materials. Specifically, dental materials include dental curable compositions of dental restorative filling materials such as a composite resin; indirect dental restorative materials for inlay, onlay, crown, and bridge; dental cement; denture materials; and the like.

In particular, the organic-inorganic composite filler is suitable for a filler to be added to dental composite restorative materials such as dental, restorative filling materials and indirect dental restorative materials. In the applications of these dental composite restorative materials, the surface of a cured product is often polished in use. In this case, macro voids in the inorganic aggregate particles inside the organic-inorganic composite filler, when present, are exposed, with the result that there significantly arises a problem with the discoloration resistance. However, the organic-inorganic composite filler of the present invention does not cause such a problem.

REFERENCE SIGNS LIST

1; ORGANIC-INORGANIC COMPOSITE FILLER
2; INORGANIC PRIMARY PARTICLE
3; ORGANIC RESIN PHASE
4; AGGREGATION GAP (MICROPORE)
5; INORGANIC PRIMARY PARTICLE COVERED WITH ORGANIC RESIN PHASE
6; MACRO VOID
L; LENGTH OF AT LEAST 1 μm

DESCRIPTION OF EMBODIMENTS (Organic-Inorganic Composite Filler)

An organic-inorganic composite filler of the present invention includes inorganic aggregate particles formed by aggregation of inorganic primary particles with an average particle diameter of 10 to 1000 nm, in which the surface of each inorganic primary particle is covered with an organic resin phase, with which the inorganic primary particles are bonded to each other. The organic resin phase incompletely fills all spaces among the inorganic primary particles.

Micropores resulting from aggregation gaps among the inorganic primary particles are formed between parts or the organic resin phase that covers the surfaces of a large number of she inorganic primary particles. Specifically, in the aggregation gaps among the inorganic primary particles covered with the organic resin phase, micropores with a pore diameter in the range of 1 to 500 nm are formed having a volume of 0.01 to 0.30 cm$^3$/g as measured by a mercury intrusion technique. As described above, a polymerizable monomer added to a curable composition penetrates the aggregation gaps by capillarity. As a result, a cured resin, which is produced by curing the polymerizable monomer, is embedded in the micropores, so that a cured product of the polymerizable monomer is strongly bonded to the organic-inorganic composite filler. In other words, a so-called anchoring effect is obtained with the aid of the micropores, with the result that the curable composition added the organic-inorganic composite filler of the present invention can form a cured product with high mechanical, strength.

Figure 1:
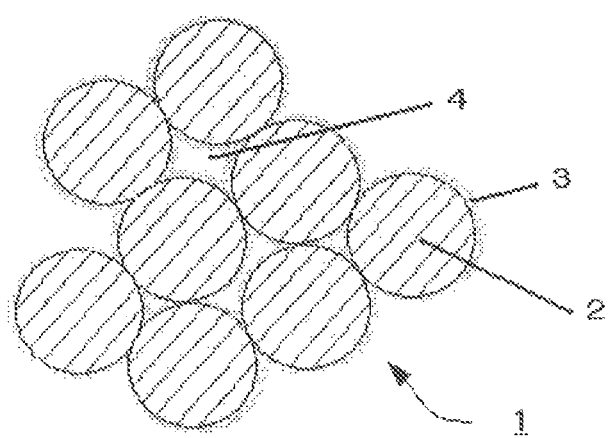
FIG. 1 is an enlarged partial view illustrating aggregation of inorganic primary particles in an organic-inorganic composite filler of the present invent ion.

Such a characteristic micropore structure of the organic-inorganic composite filler of the present invention is described in accordance with FIG. 1, which is an enlarged partial view illustrating the aggregation of the primary particles. The organic-inorganic composite filler 1 is formed by aggregation of a plurality of inorganic primary particles 2 with an average particle diameter of 10 to 1000 nm. The surfaces of the plurality of inorganic primary particles 2 are each covered with an organic resin phase 3, and the organic resin phases 3 are melted together and integrally solidified. As a result, the primary particles 2 are strongly bonded to each other through the organic resin phase 3.

The organic resin phase 3 incompletely fills all spaces in gaps formed by aggregation of the inorganic primary particles, so that aggregation, gaps 4 remain. Among ail pores formed of the aggregation gaps 4, a total volume of micropores with a pore diameter in the range of 1 to 500 nm is from 0.01 to 0.30 cm$^3$/g, preferably from 0.03 to 0.20 cm$^3$/g.

In the present invention, the micropore volume of the organic-inorganic composite filler is a value measured by a mercury intrusion technique. The measurement of the micropore volume by a mercury intrusion technique is performed as described below.

Firstly, a predetermined amount of the organic-inorganic composite filer to be measured is placed in a measurement cell. Subsequently, with the use of a mercury porosimeter, the amount of injected mercury is measured at a pressure corresponding to each diameter of pores formed in the aggregation gaps in the organic-inorganic composite filler. The micropore volume is then calculated by integrating the amounts of injected mercury for the respective micropores. As described above, the pore diameters of the micropores to be measured for the micropore volume measurement are in the range of 1 to 500 nm.

As described below, in a cross section passing through the center of the filler particle (central cross section) of the organic-inorganic composite filler of the present invention, there is substantially no huge void (macro void) with a maximum width of at least 1 μm. However, when inorganic aggregate particles with weak aggregation of inorganic primary particles are used for example, the resulting organic-inorganic composite filler may have, though to a lesser extent, a relatively large pore with a pore diameter of more than 500 nm and less than 1 urn. Sufficient capillarity hardly occurs in such a relatively large pore in the organic-inorganic composite filler. In this case, a polymerizable monomer contained in a curable composition, cannot sufficiently penetrate the pore. As a result, an anchoring effect with the aid of a polymer from the penetrating polymerizable monomer fails to be obtained sufficiently. Otherwise, even when the polymerizable monomer penetrates such a relatively large pore in some degree, a sufficient anchoring effect hardly occurs.

In the present invention, the presence of such a relatively large pore in the surface of the organic-inorganic composite filler is acceptable. However, the relatively huge pore more than 500 nm is not counted as a pore to be measured when the above mentioned micropore volume is determined. On the other hand, it is difficult for a mercury intrusion technique to measure the volume of micropores with a pore diameter of less than 1 nm. Furthermore, when the organic resin phase is formed, micropores with a small diameter are closed, it is therefore considered that such closed micropores are difficult to remain as micropores, and even when such closed micropores remain as micropores, the anchoring effect will not occur sufficiently. In the present, invention, therefore, micropores with a pore diameter out of the above mentioned pore diameter range are not counted as micropores to be measured for the micropore volume.

When an organic-inorganic composite filler with a micropore volume less than 0.01 cm$^3$/g is added to a curable composition, only a small amount of polymerizable monomer penetrates the micropores. As a result, a sufficient anchoring effect is not obtained, so that the resulting cured product has low mechanical strength.

On the other hand, when the micropore volume is more than 0.30 cm$^3$/g, an organic-inorganic composite filler itself becomes brittle, and it is also difficult to produce the filler. Therefore, from the viewpoint of obtaining these effects at a higher level, the micropore volume the organic-inorganic composite filler has is preferably from 0.03 to 0.2 cm$^3$/g.

The average pore diameter of the micropores formed in the organic-inorganic composite filler is, but not particularly limited to, preferably from 3 to 300 nm, in particular, preferably from 10 to 200 nm. When the organic-inorganic composite filler has the average pore diameter within the above range, the micropore volume thereof is within the above mentioned micropore volume in many cases. The average pore diameter of the micropores formed of the aggregation gaps refers to a median pore diameter, which is determined based on the pore volume distribution of the pores with a pore diameter in the range of 1 to 500 nm as measured by a mercury intrusion technique.

The average particle diameter (particle size) of the organic-inorganic composite fillers of the present invention is preferably from 3 to 100 μm, more preferably from 5 to 70 μm. When the average particle diameter is less than 3 μm, a dental curable composition may be loaded with the filler at a low loading rate. As a result, the cured product of the dental curable composition obtained has low mechanical strength, or the dental curable composition has high viscosity, so that the handling property during dental treatment is degraded. When the average particle diameter is more than 100 μm, the dental curable composition has low fluidity. As a result, the handling property during dental treatment is degraded.

The average particle diameter of the organic-inorganic composite fillers refers to a median diameter, which is determined based on a particle size distribution obtained by laser diffraction-scattering method. The sample to be subjected to the measurement is prepared by uniformly dispersing 0.1 g of the organic-inorganic composite filler in 10 ml of ethanol.

The most distinctive feature of the organic-inorganic composite filler of the present invention with such particle properties is that the above mentioned micropores are formed in the aggregation gaps among the inorganic primary particles, and when observing the central cross section of the particles, there is substantially no huge void (macro void) with a maximum width of at least 1 μm. As described above, when a macro void remains inside the organic-inorganic composite filler, adding this organic-inorganic composite filler into a dental curable composition results in insufficient discoloration resistance. However, using the organic-inorganic composite filler of the present invention does not cause such a disadvantage.

Figure 2:
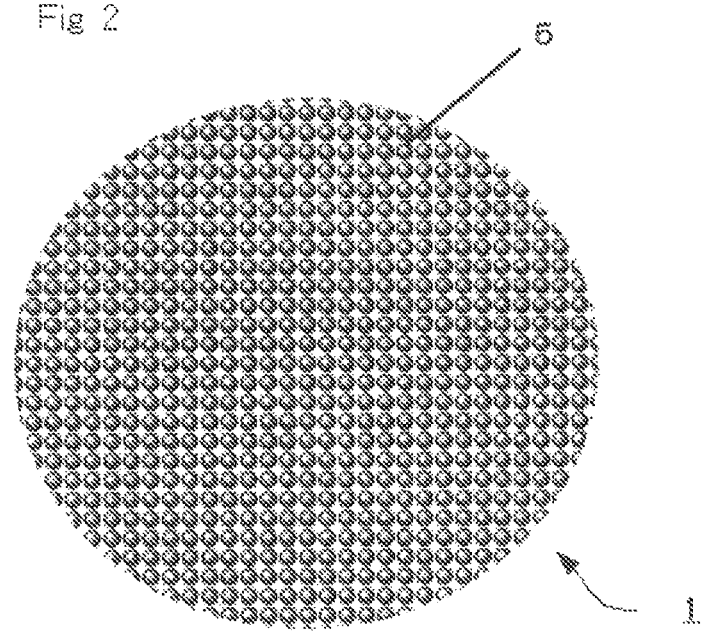
FIG. 2 is a schematic view of a central cross section illustrating an arrangement of inorganic primary particles in a spherical organic-inorganic composite filler of the present invention.
Figure 3:
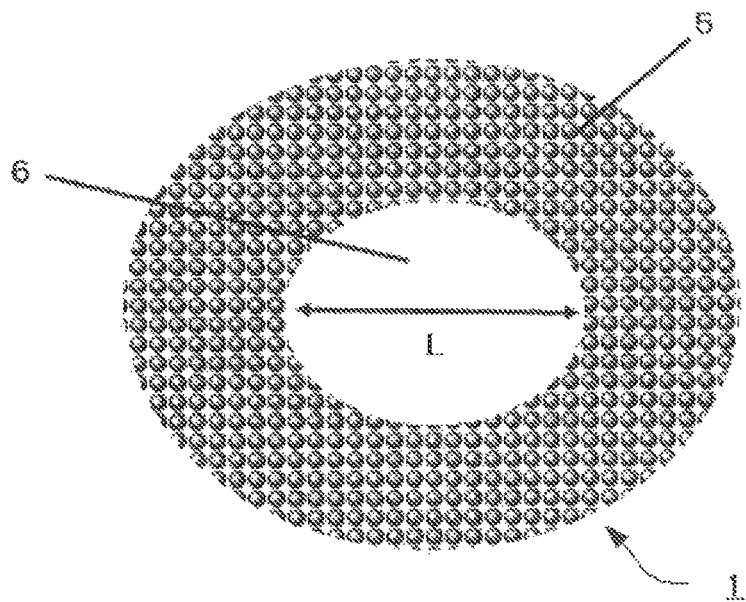
FIG. 3 is a schematic view of a central cross section of spherical organic-inorganic composite filler particles with a macro void, obtained in Comparative Example 2.
Figure 4:
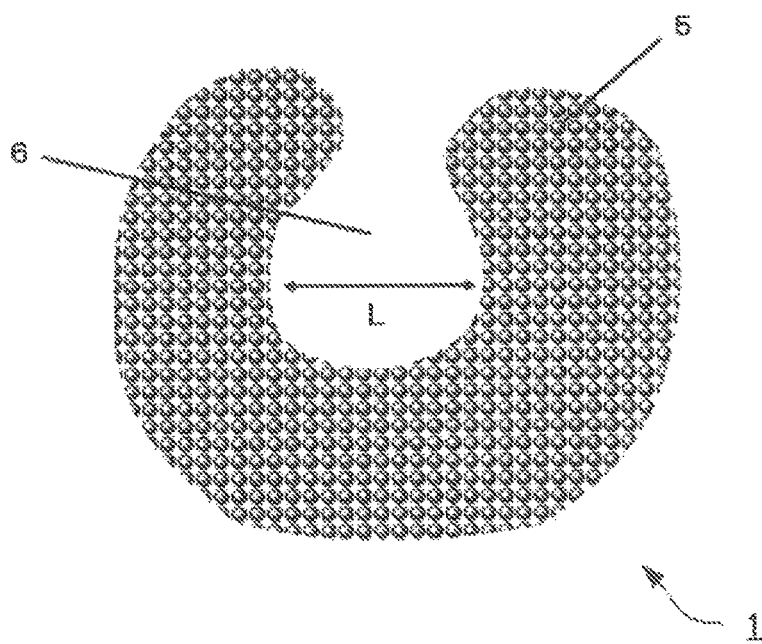
FIG. 4 is a schematic view of a central cross section of organic-inorganic composite filler particles with a dimpled macro void.

FIG. 2 is a central cross section view illustrating a representative aspect of the organic-inorganic composite filler with no macro void, of the present invention. As comparative views to FIG. 2, FIGS. 3 and 4 are represented, in each of which a specific example of an organic-inorganic composite filler having a macro void is illustrated. FIG. 3 is a central cross section view or a spherical organic-inorganic composite filler obtained in Comparative Example 2 as described below, in which central cross section there remains a macro void 6. In other words, this organic-inorganic composite filler is a hollow filler. Reference character L represents a maximum length of the macro void 6 in the central cross section, the value of which is more than 1 μm. Reference number 5 represents each of inorganic primary particles that constitute the organic-inorganic composite filler, the inorganic primary particles aggregating to have an arrangement nearly close to a close-packed structure. FIG. 4 illustrates a central cross section of a dimpled organic-inorganic composite filler. This organic-inorganic composite filler 1 has a dimpled shape with a part of the nearly spherical filler surface greatly caving inside the filler. In the central cross section, there remains a macro void represented by reference number 6 in the same way.

In the present invention, the observation of the central cross sections of organic-inorganic composite filler particles is carried out according to methods as described below.

First of all, the organic-inorganic composite filler to be observed is mixed into a liquid embedding resin, and the mixed embedding resin is cured. Then, the resulting cured product is cut with a diamond knife to form a cut surface, which is so smooth as to allow the observation of the cross section of the organic-inorganic composite filler. Subsequently, the cut surface is photographed by a scanning electron microscope at magnifications of 50 to 200 times. In an obtained image, a large number of the cross sections of organic-inorganic composite fillers are observed. Out of these cross sections, based on the average particle diameter of the organic-inorganic composite fillers calculated according to a method as described below, 100 cross sections are randomly selected and observed, in which the organic-inorganic composite filler diameter has a length in the range of 90 to 110% of the average particle diameter. It can be considered that these 100 selected cross sections are those substantially passing through the center.

Therefore, a cross section selected as described above is defined as the central cross section hereinafter.

In the organic-inorganic composite filler of the present invention, it is most preferred that there appeared no macro void at all with a maximum width of at least 1 μm in the observation of 100 central cross sections of the fillers. However, such a case is allowable as including no substantial macro void where, into a cured product of a dental curable composition containing the organic-inorganic composite filler of the present invention, an organic-inorganic composite filler with a few number of macro voids is mixed, but there arises substantially no problem with the discoloration resistance. Specifically, such particles are allowable as including no substantial macro void, in a case where based on the observation of the 100 central cross sections of the particles, there preferably appeared at most 10 voids with at least 1 μm, more preferably at most 5, in particular preferably at most 4.

Any liquid resin for use in embedding the organic-inorganic composite filler may be used, as long as the resin can be cured after the mixing with the organic-inorganic composite filler, and the cured product thereof has a sufficient hardness to be out. Examples of the resin may include polymerizable monomer as described below and epoxy resin.

The appearance of the organic-inorganic composite filler of the present invention is not particularly limited, but has a spherical or nearly spherical shape by being produced according to a method as described below. The term "nearly spherical" means that the average degree of symmetry is at least 0.6.

The appearance (average degree of symmetry) of the organic-inorganic composite filler is measured with the use of a scanning or transmission electron microscope. Specifically, performing image analysis of she image of the organic-inorganic composite fillers gives a maximum, length and minimum width of the organic-inorganic composite fillers, from which the average degree of symmetry is determined. The electron microscopy image to be used has a sharp contrast so that the contour of each particle can be identified.

The image analysis is performed with the use of an image analysis software that enables at least the measurement of a maximum particle length and minimum width. Randomly selected 100 inorganic aggregate particles are measured for a maximum particle length and minimum width by the above mentioned method, and the average degree of symmetry of the inorganic aggregate particles are calculated from the formula below.

$$\text{Average degree of symmetry} = \frac{\sum_{i=1}^{n} Bi/Li}{n} \qquad \text{[Mathematical Formula 1]}$$

In the formula, (n) is defined as the number of aggregate particles, the long diameter (Li) is defined as the maximum length of the i-th aggregate particle, and the minimum width (Bi) is defined as the diameter in the direction perpendicular to the long diameter.

The average particle diameter of the inorganic primary particles is from 10 to 1000 nm, preferably from 40 to 800 nm, more preferably from 50 to 600 nm. When the inorganic primary particles have an average particle diameter of less than 10 nm, it is difficult to form micropores with the micropore volume being characteristic of the present invention. Furthermore, the openings of the micropores are more likely to be blocked by the organic resin phase in the process of producing the organic-inorganic composite filler. As a result, she resulting filler is more likely to have air bubble inclusions. When the organic-inorganic composite filler has air bubble inclusions, the cured product of a curable composition added the organic-inorganic composite filler will have low transparency.

On the other hand, when an organic-inorganic composite filler with the average particle diameter of inorganic primary particles more than 1000 nm are used to form a dental composite restorative material, or the like, the resulting cured product is likely to have low polishability, which makes it difficult to obtain the cured product with a smooth surface.

The shape of the inorganic primary particles is not particularly limited, but spherical, nearly spherical, or irregular form particles may be used. The organic-inorganic composite filler should provide high wear resistance and surface smoothness, and nave uniform micropores, as well as should be less likely to have air bubble inclusions, which are caused by the blocking of the openings of the micropores with the organic resin phase. From these points of view, the inorganic primary particles are preferably spherical or nearly spherical. The term "nearly spherical" means that the average degree of symmetry is at least 0.6. The average degree of symmetry is more preferably at least 0.7, in particular, preferably at least 0.8.

In the present invention, the primary particle diameter of the inorganic particle is measured with the use of a scanning or transmission electron microscope. Specifically, performing image analysis of the image of the organic-inorganic composite filler determines the circle equivalent diameter of each inorganic primary particle (the diameter of a circle having the same area as that of the object particle). The electron microscopy image to be used has a sharp contrast so that the contour of each particle can be identified.

The image analysis is performed, with the use of an image analysis software that enables at least the measurement of a particle area, maximum, particle length, and minimum width. Randomly selected 100 inorganic primary particles are measured for a primary particle diameter (circle equivalent diameter), maximum particle length, and minimum width by the above mentioned method, and the average particle diameter and average degree of symmetry of the inorganic primary particles are calculated from the formulae below.

$$\text{Average particle diameter: } X = \sqrt[3]{\frac{\sum_{i=1}^{n} X_i^3}{n}} \text{ Average volume diameter} \qquad \text{[Mathematical Formula 2]}$$

n: the number of observed particles
Xi: the particle diameter (diameter) of the i-th particle $$\text{Average degree of symmetry} = \frac{\sum_{i=1}^{n} Bi/Li}{n} \qquad \text{[Mathematical Formula 3]}$$

In the formula, (n) is defined as the number of particles, the long diameter (Li) is defined as the maximum length of the i-th particle, and the minimum width (Bi) is defined as the diameter in the direction perpendicular to the long diameter.

A material or the inorganic primary particle is not particularly limited, but any material used as a filler in conventional dental curable compositions may be used. Specific examples thereof include elemental metals selected from Group I, II, III and IV, and transition metals of the periodic table; oxides or complex oxides of these metals; salts of these metals, such as fluorides, carbonates, sulfates, silicates, hydroxides, chlorides, sulfites, and phosphates of these metals; and composites of these salts of metals. Preferably used are metal oxides such as amorphous silica, quartz, alumina, titania, zirconia, barium, oxide, yttrium oxide, lanthanum oxide, and ytterbium oxide; silica-based complex oxides such as silica-zirconia, silica-titania, silica-titania-barium oxide, and silica-titania-zirconia; glass such as borosilicate glass, aluminosilicate glass, and fluoroaluminosilicate glass; metal fluorides such as barium fluoride, strontium fluoride, yttrium fluoride, lanthanum fluoride, and ytterbium fluoride; inorganic carbonates such as calcium carbonate, magnesium carbonate, strontium carbonate, and barium carbonate; and metal sulfates such as magnesium sulfate and barium sulfate.

Among these materials, metal oxides and silica-based complex oxides are preferably fired, at high temperature so that dense materials can be obtained. To increase the densification effect, a small amount of an oxide of a metal of Group I of the periodic table, such as sodium, is preferably included.

Among inorganic primary particles of the above mentioned materials, silica-based complex oxide particles have refractive indices capable of being controlled easily. These particles are also in particular preferred, because they have a large amount of silanol groups on their surfaces, so that their surfaces can be easily modified by using a silane coupling agent or the like.

Particles of silica-zirconia, silica-titania, silica-titania-barium oxide, silica-titania-zirconia or the like as listed above are preferred, because they have strong X-ray imaging properties. Furthermore, silica-zirconia particles are most preferred, because they can form a cured product with higher wear resistance. Metal fluorides such as barium fluoride, strontium fluoride, yttrium fluoride, lanthanum fluoride, and ytterbium fluoride are also preferred, because of their strong X-ray imaging properties.

These inorganic primary particles may be produced by any publically known method. For example, inorganic oxide primary particles, complex oxide primary particles, or the like may be produced by any of a wet method, dry method, and sol-gel method. The inorganic primary particles are preferably produced by a sol-gel method, considering that the sol-gel method is advantageous in industrially producing fine particles with a spherical shape and high monodispersity, and can easily control the refractive index and easily impart X-ray imaging property.

There are publically known methods for producing spherical particles of silica-based complex oxide by a sol-gel method, such as those disclosed in JP 1983-110414 A, JP 1983-151321 A, JP 1983-156524 A, and JP 1933-156526 A.

In these methods, a mixed solution containing a hydrolyzable organosilicon compound and optionally a hydrolyzable organic compound of another metal is firstly prepared. Subsequently, the mixed solution is added to an alkaline solvent, in which these organic compounds are soluble but an inorganic oxide to be produced, is substantially insoluble, and the organosilicon compound and the like are hydrolyzed. The precipitate of the inorganic oxide is separated by filtration and then dried, so that the inorganic primary particles are obtained.

The inorganic primary particles obtained by such a method may be fired at temperatures of 500 to 1000° C. after the drying, so that surface stability is provided. During firing, a part of the inorganic primary particles may aggregate. In such, a case, it is preferred that aggregate particles be dissociated into primary particles with the use of a jet mill, a vibratory ball mill or the like, and further the particle size be adjusted within the predetermined range, before use. Such a process can increase the polishability and other properties of a cured product in use as a dental composite restorative material.

The inorganic primary particles may be a mixture of two or more types of inorganic primary particles different in the average particle diameter, material, or shape.

The organic resin phase coating the surfaces of the inorganic primary particles covers the surface of each of the inorganic primary particles, and includes a cured polymer of the polymerizable monomer bonding the inorganic primary particles to each other and a water absorbing resin. This water absorbing resin is added to a dispersion of the inorganic primary particles in order not to form a macro void inside the particles when a suitable method for producing the organic-inorganic composite filler as described below is performed. As such a water absorbing resin, amp/publically known water absorbing resin may be used without limitation. The water absorbing resin is a resin which has a water absorbency of 1.0 times or more, more preferably 30 to 1000 times as much as the self weight at an end point where the sample exhibits fluidity when, water is dropped at 23° C.

The water absorbing resin used in the present invention is a natural, synthetic or semisynthetic water-soluble polymer which can dissolve in water to give a viscous water solution. Basically, the water absorbing resin is a noncrosslinked wafer-soluble polymer or oligomer. Examples of such a water absorbing resin include water-soluble polymers used in the application of high molecular coagulants with a weight-average molecular weight of 500000 to 20000000, thickeners with a weight-average molecular weight of 500000 to 5000000, dispersants and the like. Furthermore, natural water-soluble polymers and derivatives thereof are included.

Specific examples of such a water absorbing resin include starch based, water absorbing resins such as starch-acrylonitrile graft copolymer, starch-acrylic acid graft copolymer, and starch-acrylate salt graft copolymer; cellulose based water absorbing resins such as cellulose-acrylonitrile graft copolymer and carboxymethyl cellulose; other polysaccharide based water absorbing resins such as hyaluronic acid; polyvinyl alcohol based water absorbing resins such as polyvinyl alcohol and ethylene-vinylalcohol copolymer; acrylate based water absorbing resins such as sodium polyacrylate and sodium salt of acrylic acid-vinyl alcohol copolymer; acrylamide based water absorbing resins such as polyacrylamide and N-substituted acrylamide; and polyether based compounds such as polyethylene glycol and polyethylene oxide.

Among the above polymers, acrylate based water absorbing resins are preferred because of their tough strength. From the viewpoint of the biological safety, polyacrylic acids or partial or complete sodium salts of polyacrylic acid are in particular preferred. The polymer has a weight-average molecular weight of preferably 2000 to 20000000, more preferably 6000 to 5000000.

In the organic resin phase, the content of the water absorbing resin relative to the cured polymer of the polymerizable monomer is generally, based on 100 parts by mass of the cured polymer of the polymerizable monomer, from 0.05 to 50 parts by mass, more preferably from 0.5 to 25 parts by mass.

Examples of the polymerizable monomer used to form the organic resin phase include each of the monomers shown in sections A to D as described below.

A. Monofunctional Vinyl Monomer

Examples of monofunctional vinyl monomer include methacrylates such as methyl methacrylate, ethyl methacrylate, isopropyl methacrylate, hydroxyethyl methacrylate, tetrahydrofurfuryl methacrylate, and glycidyl methacrylate, and acrylates corresponding to these methacrylates; acrylic acid, methacrylic acid, p-methacryloyloxybenzoic acid, N-2-hydroxy-3-methacryloyloxypropyl-N-phenylglycine, 4-methacryloyloxyethyltrimellitic acid, and anhydrides thereof, 6-methacrylcyloxyhexamethylenemalonic acid, 10-methacryloyloxydecamethylenemalonic acid, 2-methacryloyloxyethyldihydrogenphosphate, 10-methacryloyloxydecamethylenedihydrogenphosphate, and 2-hydroxyethylhydrogenphenylphosphonate.

B. Bifunctional Vinyl Monomer

B-1 Aromatic Compound Monomer

Examples of aromatic compound monomer include 2,2-bis(methacryloyloxyphenyl) propane, 2,2-bis[4-(3-methacryloyloxy)-2-hydroxypropoxyphenyl]propane, 2,2-bis(4-methacryloyloxyphenyl)propane, 2,2-bis(4-methacryloyloxypolyethoxyphenyl)propane, 2,2-bis(4-methacryloyloxydiethoxypnenyl) propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2-(4-metnacryloyloxydiethoxyphenyl)-2-(4-methacryioyloxydiethoxyphenyl)propane, 2-(4-methacryloyloxydiethoxyphenyl)-2-(4-methacryloyloxyditriethoxyphenyl)propane. 2-(4-methacryloyloxydipropoxyphenyl)-2-(4-methacryloyloxytriethoxyphenyl)propane, 2,2-bis(4-methacryloyloxypropoxyphenyl) propane, 2,2-bis(4-methacryloyloxyisopropoxyphenyl) propane, and acrylates corresponding to these methacrylates; and diadducts obtained by the addition reaction between an OH group-containing vinyl monomer such as methacrylates such as 2-hydroxyethyl methacrylate, 2-hydroxypropyl methacrylate, and 3-chloro-2-hydroxypropyl methacrylate, or acrylates corresponding to these methacrylates, and an aromatic group-containing diisocyanate compound such as diisocyanatomethyl benzene and 4,4'-diphenylmethane diisocyanate.

B-2 Aliphatic Compound Monomer

Examples of aliphatic compound monomer include ethylene glycol dimethacrylate, diethylene glycol dimethacrylate, triethylene glycol dimethacrylate, butadiene glycol dimethacrylate, neopentyl glycol dimethacrylate, propylene glycol dimethacrylate, 1,3-butanediol dimethacrylate, 1,4-butanediol dimethacrylate, 1,6-hexanediol dimethacrylate, and acrylates corresponding to these methacrylates; diadducts obtained by the addition reaction between an OH group-containing vinyl monomer such as methacrylates such as 2-hydroxyethyl methacrylate, 2-hydroxypropyl methacrylate, and 3-chloro-2-hydroxypropyl methacrylate, or acrylates corresponding to these methacrylates, and a diisocyanate compound such as hexamethylene diisocyanate, trimethylhexamethylene diisocyanate, diisocyanatomethylcyclohexane, isophorone diisocyanate, and methylene bis(4-cyclohexylisocyanate); and acrylic anhydride, methacrylic anhydride, 1,2-bis(3-methacryloyloxy-2-hydroxypropoxy)ethyl, and di(2-methacryloyloxypropyl)phosphate.

C. Trifunctional Vinyl Monomer

Examples of trifunctional vinyl monomer include methacrylates such, as trimethylolpropane trimethacrylate, trimethylolethane trimethacrylate, pentaerythritol trimethacrylate, and trimethylolmethane trimethacrylate, and acrylates corresponding to these methacrylates.

D. Tetrafunctional Vinyl Monomer

Examples of tetrafunctional vinyl monomer include pentaerythritol tetramethacrylate, pentaerythritol tetraacrylate, and diadducts obtained by the addition reaction between, a diisocyanate compound such as diisocyanatomethylbenzene, diisocyanatomethylcyclohexane, isophorone diisocyanate, hexamethylene diisocyanate, trimethylhexamethylene diisocyanate, methylenebis(4-cyclohexylisocyanate), 4,4-diphenylmethanediisocyanate, and tolylene-2,4-diisocyanate, and glycidol dimethacrylate.

Among the above mentioned monomers, polymerizable monomers having compatibility with an organic solvent are preferred. In addition, (meth)acrylic polymerizable monomers are preferred, because they can form polymers with high mechanical strength or biological safety. Furthermore, bifunctional or polyfunctional polymerizable monomers are preferred, and bifunctional to tetrafunctional polymerizable monomers are more preferred, because they have high polymerizability, can form cured products with particularly high mechanical properties, or the like.

One of these polymerizable monomers may be used alone, or two or more different types of these polymerizable monomers may be used in combination.

When the organic-inorganic composite filler of the present invention is used as a filler for a dental curable composition, the polymerizable monomer is preferably selected so that there will be a difference of 0.1 or less between the refractive indices of the resulting polymer and the inorganic primary particles. When the monomer is selected in such a manner, sufficient transparency can be imparted to the resulting organic-inorganic composite filler. Furthermore, when the organic-inorganic composite filler is added to a dental curable composition, the polymerizable monomer is preferably selected so that there will be a difference of 0.1 or less between the refractive indices of the organic-inorganic composite filler and a polymer of a polymerizable monomer added to the dental curable composition. When the monomer is selected in such a manner, a transparent cured product can be obtained from the dental curable composition.

In the organic-inorganic composite filler, the content of the organic resin phase is generally, based on 100 parts by mass of the inorganic primary particles, from 1 to 40 parts by mass, preferably from 5 to 25 parts by mass. The content of the organic resin phase can be determined from a mass reduction obtained by thermogravimetry-differential thermal analysis.

(Method for Producing Organic-Inorganic Composite Filler)

Hereinafter, a description is made of methods for producing the organic-inorganic composite filler of the present invention. Methods for producing the organic-inorganic composite filler of the present invention are not limited to specific methods. However, it is generally difficult to produce the organic-inorganic composite filler of the present invention by using conventional methods for producing an organic-inorganic composite filler.

Specifically, the organic-inorganic composite filler of the present invention is preferably produced by the method described below. This method essentially includes using inorganic primary particles with an average particle diameter of 10 to 1000 nm as a starting material and performing the steps described below.

(1) The step of spray drying an aqueous suspension of the inorganic primary particles with an average particle diameter of 10 to 1000 nm containing a water absorbing resin to granulate the inorganic primary particles, so that inorganic aggregate particles are formed in which surfaces of the inorganic primary particles are coated with the water absorbing resin, (2) The step of immersing the formed inorganic aggregate particles with a polymerizable monomer solution containing 100 parts by mass of an organic solvent, 3 to 70 parts by mass of a polymerizable monomer, and an effective amount of a polymerisation initiator, (3) The step of removing the organic solvent from the immersed inorganic aggregate particles, (4) The step of polymerizing and curing the polymerizable monomer with which the inorganic aggregate particles are impregnated.

In the above mentioned producing method, firstly, the inorganic primary particles are granulated by spray drying an aqueous suspension of the inorganic primary particles with an average particle diameter of 10 to 1000 nm containing a water absorbing resin. As a result, inorganic aggregate particles are obtained in which the water absorbing resin is attached to the surfaces of the inorganic primary particles. In general, the inorganic primary particles are preferably produced by a sol-gel method, because the resultants have high monodispersity. When the inorganic primary particles are produced by a sol-gel method including a dry process or a firing process, they may partly aggregate during the process. In this case, it may be difficult to readily subject the inorganic primary particles to the above mentioned spray drying. In addition, it is common that the inorganic primary particles produced by a wet method or a dry method (in particular a wet method) are more severely aggregated. In such a case, the aggregated inorganic primary particles may be ground and then subjected to the spray drying as a raw material.

The method for granulation by spray drying includes spraying the aqueous suspension of the inorganic primary particles into droplets, for example, with the use of a fast gas stream, and bringing the sprayed droplets into contact with high-temperature gas to volatilize the aqueous medium. As the aqueous medium is volatilized, a large number of the inorganic primary particles dispersed in the droplets are aggregated to form substantially a single inorganic aggregate particle. The particle diameter or particle size distribution of the aggregate particles can be controlled according to the type of spray or the spray conditions.

The method for granulation by spray drying is advantageous; because it can produce inorganic aggregate particles with a narrow particle size distribution and an average particle diameter of 3 to 100 μm, which particles are desirable as a raw material for the organic-inorganic composite filler of the present invention. Furthermore, when the inorganic aggregate particles are produced by this method for granulation, inside the inorganic aggregate particles, aggregation gaps are spontaneously formed with a micropore volume of 0.015 to 0.35 $cm^3/g$, more preferably 0.15 to 0.30 $cm^3/g$, as measured by a mercury intrusion technique. When the organic-inorganic composite filler of the present invention is produced using inorganic aggregate particles with this micropore volume, the resulting organic-inorganic composite fillers generally have thereinside a micropore volume of 0.01 to 0.30 $cm^3/g$, more preferably 0.03 to 0.20 $cm^3/g$. Therefore, using the method for granulation by spray drying can efficiently produce the organic-inorganic composite filler with the micropore volume of the present invention.

In general, the micropore volume of the inorganic aggregate particles increases with narrowing the particle size distribution of the inorganic primary particles used to form the inorganic aggregate particles. On the other hand, the micropore volume thereof decreases with broadening the particle size distribution of the inorganic primary particles. Furthermore, combining two or more types of the inorganic primary particles with different average particle diameters can reduce the micropore volume of the inorganic aggregate particles. In addition, combining two or more types of the inorganic primary particles in such, a ratio that close-packing can be achieved can further reduce the micropore volume in the inorganic aggregate particles.

In the producing method of the present invention, in spray drying the aqueous suspension of the above mentioned inorganic primary particles, the aqueous suspension containing the water absorbing resin is used. The presence of the water absorbing resin in the aqueous suspension makes it difficult for the resulting inorganic aggregate particles to form a macro void thereinside. As a result, the organic-inorganic composite filler produced using the inorganic aggregate particles also is without the macro void inside the filler.

The reason why inclusion of the water absorbing resin in the aqueous suspension of the inorganic primary particles results in the inorganic aggregate particles being without a macro void is presumably based on the following mechanism.

When an aqueous suspension of the inorganic primary particles not containing a water absorbing resin is spray dried, volatilization of an aqueous medium occurs at the surface of the sprayed droplet in the early stage of drying, and subsequently the volatilization progresses toward the inner side of the particles at once. Therefore, at the beginning when the surface of the sprayed droplet is dried, a hard shell portion with a hollow and spherical shape is formed near the surface of the particles, and subsequently the drying rapidly progresses from she shell portion to the center of the droplet. The shape of the shell pore ion is maintained as it is because of the hardness, while she drying progresses. As a result, it is believed that the concentration of the inorganic primary particles is low when the vicinity of the center of the droplet is dried, so that a macro void is formed inside the shell portion.

It seems that when a larger macro void is formed inside she inorganic aggregate particles according to the above mentioned mechanism, deformation of the shell occurs, so that the shape of the inorganic aggregate particles further change to a dimpled or toroidal shape.

On the other hand, it seems that, when the water absorbing resin is contained in the aqueous suspension of the inorganic primary particles, the water absorbing resin affects the aqueous medium so as to lower the drying rate. In other words, the aqueous medium is mildly dried at the surface of the sprayed droplet in the early stage of drying. As a result, the inorganic primary particles are dried while moving toward the center of the droplet without forming the shell near the surface. Therefore, it is speculated that the presence of the water absorbing resin will lead to the progress of uniform drying inside the particles.

The inorganic aggregate particles obtained by spray drying may have any of a spherical shape, nearly spherical shape, elliptical shape, dimpled shape, or toroidal shape, but preferably a spherical shape.

In the present invention the amount of the water absorbing resin contained in the aqueous suspension of the inorganic primary particles is, not particularly limited but, preferably from 0.01 to 10 parts by mass, in particular preferably from 0.05 to 5 parts by mass, based on 100 parts by mass of the inorganic primary particles. When the content of the water absorbing resin is 0.01 parts by mass or more based on 100 parts by mass of the inorganic primary particles, the rapid drying of the sprayed droplet is prevented, so that it is difficult for the inorganic aggregate particles to form a macro void thereinside. Additionally, because the content of the water absorbing resin is 10 parts by mass or less, the resulting organic-inorganic composite filler may have nigh mechanical properties.

Thus, when the water absorbing resin is added to the aqueous suspension, preferably 0.01 to 10 parts by mass, more preferably 0.05 to 5 parts by mass of the water absorbing resin is contained in the resulting inorganic aggregate particles, based on 100 parts by mass of the inorganic primary particles.

In the present invention, she preparing method for the aqueous suspension of the inorganic primary particles is not particularly limited. For example, a method is preferred that includes dispersing inorganic primary particles in an aqueous medium with the use of a mixer such as a bead mill, and further adding a water-absorbing resin therein in order to prepare a slurry aqueous suspension.

Water is used as the liquid medium for use in the suspension of the inorganic primary particles. An organic solvent may be added, such as ethanol, isopropyl alcohol, chloroform, and dimethylformamide, as needed.

In addition, the concentration of the inorganic primary particles in the aqueous suspension is not limited, as long as the aqueous suspension can be atomized in the spray drying. However, from the viewpoint of preventing the formation of a macro void, the concentration of the inorganic primary particles is preferably from 5 to 50% by mass, more preferably from 20 to 45% by mass.

In the present invention, a description is made of preferred spray drying methods below. A method includes spraying the aqueous suspension prepared by the above mentioned method as fine droplets with the use of a fast gas stream and drying the same. Another method includes allowing drops of the aqueous suspension to fall on a rotating disk so that the aqueous suspension is flicked and sprayed by the centrifugal force and dried. The rotational speed of the rotating disk is generally from 1000 to 50000 rpm. The droplet diameter is so controlled that inorganic aggregate particles with the desired average particle diameter are obtained, taking info account the diameter of primary particles of the inorganic particles.

When the sprayed aqueous suspension is immediately dried with the use of nigh-temperature air, inert gas or the like, inorganic aggregate particles with uniform size are obtained. The temperature of the gas used in the drying is generally from 60 to 300° C., preferably from 80 to 250° C.

A slight amount of the solvent, which is used in the preparation of the aqueous suspension, may still remain in the inorganic aggregate particles obtained by the above mentioned spray drying. Therefore, after the spray drying, the resulting inorganic aggregate particles are preferably dried under vacuum. The vacuum drying is generally performed for a time period of 1 to 43 hours at a temperature of 20 to 150° C. under a reduced pressure of 0.01 to 100 hPa or less.

When inorganic primary particles with an average particle diameter of 10 to 1000 nm are granulated by a spray drying method, inorganic segregate particles can be produced having aggregation gaps with a micropore volume of 0.015 to 0.35 $cm^3/g$, more preferably 0.15 to 0.30 $cm^3/g$. In such inorganic aggregate particles, the water absorbing resin is partially attached to each of the inorganic primary particles.

The inorganic primary particles aggregated, near the surface of the inorganic aggregate particles generally have an arrangement close to a hexagonal close-packed structure. When the inorganic primary particles are arranged along the surface of the inorganic aggregate particles to form a structure close to a hexagonal close-packed structure, the micropores are formed of the aggregation gaps among the adjacent inorganic primary particles. Such micropores usually have an average pore diameter of 5 to 330 nm, more usually 20 to 300 nm.

The micropore volume and the average pore diameter of the inorganic aggregate particles can be determined by the same measurement method as in the case of the organic-inorganic composite filler described above.

The inorganic aggregate particles to be used in the production of the organic-inorganic composite filler are preferably surface-treated with a hydrophobing agent so as to have increased wettability to the polymerizable monomer. Any publically known hydrophobing agent may be used without limitation. Preferred examples of the hydrophobing agent include silane coupling agents such as vinyltriethoxysilane, vinyltrimethoxysilane, vinyl-tris(β-methoxyethoxy)silane, γ-methacryloyloxypropyltrimethoxysilane, κ-methacryloyloxydodecyltrimethoxysilane, β-(3,4-epoxycyclohexyl)-ethyltrimethoxysilane, γ-glycidoxypropyl-trimethoxysilane, N-β-(aminoethyl)-γ-aminopropyl-trimethoxysilane, γ-ureidopropyl-triethoxysilane, γ-chloropropyitrimethoxysilane, methyltrimethoxysilane, ethyltrimethoxysilane, and methyltriefhoxysilane, and titanate coupling agents.

The amount of the hydrophobing agent used for hydrophobing the inorganic aggregate particles is not particularly limited but may be set at an optimal value after a preliminary experiment is performed to check the mechanical properties and other properties of the organic-inorganic composite filler to be obtained. For example, the hydrophobing agent is preferably used in an amount of 1 to 30 parts by mass based on 100 parts by mass ox the inorganic primary particles.

The surface treatment method is not particularly limited, but any publically known surface treatment method may be used without limitation. For example, a typical treatment method therefor includes dispersing and mixing inorganic particles and a hydrophobing agent in a suitable solvent with the use of a ball mill or the like, drying the mixture with the use of an evaporator or air drying, and then beating the dried mixture at 50 to 150° C. Another treatment method therefor includes heating and refluxing inorganic particles and a hydrophobing agent in a solvent such as alcohol for about several hours. A further treatment method therefor includes graft-polymerizing a hydrophobing agent onto particle surfaces.

The surface treatment may be performed on the inorganic primary particles or the inorganic aggregate particles. When the inorganic aggregate particles are produced by the above mentioned spray drying, it is efficient to perform the surface treatment at the same time in this process.

Subsequently, the inorganic aggregate particles produced as described above are immersed in a polymerizable monomer solution containing 100 parts by mass of an organic solvent, 3 to 70 parts by mass of a polymerizable monomer, and an effective amount of a polymerization initiator. As a result, the polymerizable monomer solution penetrates the inside of the inorganic aggregate particles through the aggregation gaps in the inorganic aggregate particles by capillarity. In this case, because the polymerizable monomer is diluted with the organic sol vent, the liquid can highly penetrate by capillarity. As a result, even deeper parts of the aggregation gaps are loaded with the polymerizable monomer solution. In addition, the water absorbing resin attached to the surfaces of the inorganic primary particles is dissolved in and mixed with the polymerizable monomer solution at that time, in case where the water absorbing resin has a solubility in the organic solvent or polymerizable monomer used. Whereas, the water absorbing resin remains attached to the inorganic, primary particles at that time, in case where the water absorbing resin has no solubility in the polymerizable monomer solution. In either case, by removing the organic solvent and polymerizing the polymerizable monomer using the methods as described below, the water absorbing resin is added to a cured product of the polymerizable monomer, and thus becomes part of the organic resin phase.

The content of the polymerizable monomer in the polymerizable monomer solution based on the amount of the organic solvent should be controlled in the above range. When the content of the polymerizable monomer is controlled in the range, the volume of the micropores formed in the aggregation gaps in the resulting organic-inorganic composite filler can be controlled in the specified range. The organic solvent contained in the polymerizable monomer solution, which penetrates the aggregation gaps in the inorganic aggregate particles, is removed before polymerization and curing of the polymerizable monomer. Micropores having a volume corresponding to the redaction in volume caused by the removal of the solvent are formed in the aggregation gaps among the inorganic primary particles. For the above mentioned reason, the content of the polymerizable monomer contained in the polymerizable monomer solution should be in the above mentioned content so that the organic-inorganic composite filler has a micropore volume in the above value range (0.01 to 0.30 $cm^3/g$).

When the polymerizable monomer content is out of the above mentioned range, the amount of the polymerizable monomer loaded in cue micropores will be excessive or insufficient. When the polymerizable monomer content is too high, fine air bubbles may be formed in the resulting organic-inorganic composite filler. Furthermore, when the polymerizable monomer content is too high, the excessive polymerizable monomer attaches to the circumference of the inorganic aggregate particles in large amounts. Unfortunately, polymerizing and curing the polymerizable monomer under such a circumstance may easily generate a block of inorganic aggregate particles bonded together. Taking such disadvantages into account, the content of the polymerizable monomer in the polymerizable monomer solution is preferably from 10 to 50 parts by mass based on 100 parts by mass of the organic solvent.

As the organic solvent contained in the polymerizable monomer solution, any publically known solvent may be used without limitation.

Examples thereof include halogen based organic solvents such as perchloroethylene, trichloroethylene, dichloromethane, and chloroform, and halogen-free organic solvents including hydrocarbon solvents such as hexane, heptane, and pentane; aromatic solvents such as benzene, toluene, and xylene; alcohol, solvents such as methanol, ethanol, 1-propanol, 2-propanol, 1-butanol, and 2-butanol; ether solvents such as diethyl ether, tetrahydrofuran, and t-butyl methyl ether; ketone solvents such as acetone, methyl ethyl ketone, and methyl isobutyl ketone; ester solvents such as ethyl formate, methyl acetate, ethyl acetate, propyl acetate, and isopropyl acetate; and the like. Among these solvents, methanol, ethanol, acetone, dichlorometnane, and the like are more preferred, from the viewpoint that they are highly volatile so that the time for the solvent removal step can be reduced, easily available and inexpensive, highly safe to the human body during the production, and the like.

The polymerization initiator contained in the polymerizable monomer solution may be any of a photopolymerization initiator, a chemical polymerization initiator, and a thermal polymerization initiator. A photopolymerization initiator or a thermal polymerization initiator is preferred, because energy such as light or heat can be applied from the outside so that the timing of the polymerization can be freely selected and the operation can be made simple. A thermal polymerization initiator is more preferred because it can be used without a process environment limitation such as light shielding or irradiation with red light.

Examples of the thermal polymerization initiator include peroxides such as benzoyl peroxide, p-chlorobenzoyl peroxide, tert-butylperoxy-2-ethylhexanoate, tert-butylperoxydicarbonate, and diisopropylperoxydicarbonate; azo compounds such as azobisisobutyronitrile; boron compounds such as tributyl borane, a partial oxide of tributyl borane, sodium tetraphenylborate, sodium tetrakis(p-fluorophenyl) borate, and tetraphenylborate triethanolamine salt; barbituric acids such as 5-butylbarbituric acid and 1-benzyl-5-phenylbarbituric acid; and sulfinate salts soon as sodium benzenesulfinate and sodium p-toluenesulfinate.

Among the above mentioned thermal polymerization initiators, azo compounds such as azobisisobutyronitrile are advantageously used, because they are highly safe during the operation, have little coloring effect on the organic-inorganic composite filler, and the like.

One of these polymerization initiators may be used alone or two or more types of these polymerization initiators may be used in combination. The amount of the polymerization initiator may be an effective amount enough to allow the polymerization to proceed. In general, based, on 100 parts by mass of the polymerizable monomer, the amount of the polymerization initiator is from 0.01 to 30 parts by mass, preferably from 0.1 to 5 parts by mass.

To impart various functions to the organic-inorganic composite filler, a publically known additive such as an ultraviolet absorbing agent, a pigment, a dye, a polymerization inhibitor, and a fluorescent, agent, may be added, to the polymerizable monomer solution.

Example of a method for allowing the polymerizable monomer solution to penetrate the inorganic aggregate particles includes a method for immersing the inorganic aggregate particles in the polymerizable monomer solution. In general, the immersion is preferably performed at room temperature under normal pressure. The mixing ratio of the polymerizable monomer solution to the inorganic aggregate particles is preferably from 30 to 500 parts by mass, more preferably 50 to 200 parts by mass of the polymerizable monomer solution to 100 parts by mass of the inorganic aggregate particles. After the mixing, the mixture is preferably allowed to stand. The temperature at which the mixture stands is not particularly limited, but generally room, temperature. The period for which the mixture stands is preferably at least 30 minutes, more preferably at least 1 hour. To accelerate the penetration of the polymerizable monomer solution into the aggregation gaps, the mixture of the polymerizable monomer solution with the inorganic aggregate particles may also be shaken and stirred, centrifuged and stirred, pressurized, reduced in pressure, or heated.

After the inorganic aggregate particles are immersed in the polymerizable monomer solution, true organic solvent is removed from the polymerizable monomer solution loaded in the aggregation gaps before the polymerizable monomer is subjected to polymerization and curing. In the removal, of the organic solvent, substantially the whole amount (generally, at least 95% by mass) of the organic solvent penetrating the aggregation gaps in the inorganic aggregate particles is removed. Visually, the removal may be performed until a coagulated product formed by adhesion of the inorganic aggregate particles to each other disappears so that a flowing powder is obtained.

Any publically known, drying method may be performed in the operation to remove the organic solvent. Examples of the drying method include drying by heating, such as convective heat transfer drying, radiant heat transfer drying, conductive heat transfer drying, and internal heat generation drying, and drying without heating, such as vacuum drying, vacuum-freeze drying, spin drying, drying with an absorbent, suction drying, press drying, and ultrasonic drying. In particular, drying by heating, vacuum drying, vacuum-freeze drying, or the like is preferred.

When vacuum drying is performed to remove the organic solvent, the reduced pressure degree may be appropriately selected taking into account the boiling point or volatility of the polymerizable monomer or the organic solvent. The reduced pressure degree is generally 100 hPa or less, preferably from 0.01 to 50 hPa, most preferably from 0.1 to 10 hPa.

When drying by heating is performed, the heating temperature may be appropriately selected depending on the boiling point of the organic solvent. When the organic solvent contains a thermal polymerization initiator as the polymerization initiator, the heating and drying should be performed at a temperature equal to or less than the polymerization-initiating temperature.

The drying method may also be a combination of the above mentioned methods. In particular, to reduce the drying time, vacuum drying is preferably used in combination with drying by heating, such as conductive heat transfer drying. The operation to remove the organic solvent may foe performed under stirring, as long as the properties of the organic-inorganic composite filler are not degraded.

After the organic solvent is removed, the polymerizable monomer is subjected to polymerization and curing. The polymerization-curing method to be used depends on the polymerizable monomer or polymerization initiator used, and therefore, an optimal method should be selected as desired. When a thermal polymerization initiator is used, the polymerization may be performed by heating, and when a photopolymerization initiator is used, the polymerization may be performed by irradiation with light having the corresponding wavelength.

When thermal polymerization is performed, the polymerization temperature depends on the polymerization initiator used, and therefore, an optimal temperature should be selected as desired. The polymerization temperature is generally from 30 to 170° C., preferably from 50 to 150° C.

When photopolymerization is performed, a light source to be used depends on the type of the polymerization initiator, and therefore, an optimal light source should be used as desired. In general, examples of the light source may include visible light sources such as a halogen lamp, LED, a xenon lamp, a high-pressure mercury lamp, a metal halide lamp, a carbon arc lamp, a tungsten lamp, a helium-cadmium laser, and an argon laser, and ultraviolet light sources such as a low-pressure mercury lamp, a xenon arc lamp, a deuterium arc lamp, a mercury-xenon arc lamp, a tungsten-halogen incandescent lamp, UV-LED, and a xenon plasma discharge tube.

According to the method described above, the organic-inorganic composite filler of the present invention can be efficiently produced.

Under si circumstance where the concentration of the polymerizable monomer in the polymerizable monomer solution is low, the above mentioned operations may be repeated twice or more. When the operations are repeated twice or more, the amount of the organic resin phase covering the surfaces of the inorganic primary particles can be gradually increased, so that the volume of the micropores formed can be controlled.

The organic-inorganic composite filler, when produced as described above using the inorganic aggregate particles with suitable particle size for the intended use, may be directly used as a final product. Such inorganic aggregate particles with suitable particle size are those produced by granulation using the above mentioned spray drying method.

When the resulting organic-inorganic composite filler has a too large particle size compared with the suitable particle size for the intended use, the organic-inorganic composite filler may be ground to have an appropriate particle size, as needed. The grinding can be performed with the use of a vibratory ball mill, a bead mill, a jet mill, or the like. Furthermore, as needed, classification may also be performed with the use of a sieve, an air classifier, a hydraulic classifier, or the like. When the grinding process is performed, the grinding step may be performed at the time point after the impregnation of the inorganic aggregate particles with the polymerizable monomer solution and the removal, of the organic solvent, and before the polymerization of the polymerizable monomer.

The organic-inorganic composite fillers may also be further surface-treated. The surface-treated organic-inorganic composite filler provides a cured product of a dental curable composition added the organic-inorganic composite filler with higher mechanical strength. A surface treatment agent and a surface treatment method may be those as described above in the surface treatment of the inorganic primary particles.

(Dental Curable Composition)

As already described above, the organic-inorganic composite filler of she present invention is particularly useful as a dental filler to be added to a dental curable composition. Such a dental curable composition contains at least a polymerizable monomer and a polymerization initiator, in addition to the organic-inorganic composite filler.

As the polymerizable monomer, any publically known polymerizable monomer used, in such a dental application may be used without limitation. In general, select ion may be made from the same group as described above in the polymerizable monomer for use in the production of the organic-inorganic composite filler. The polymerizable monomer may be added in an amount of 10 to 100 parts by mass, preferably 20 to 80 parts by mass, based on 100 parts by mass of the organic-inorganic composite filler.

As the polymerization initiator, any publically known polymerization initiator may be used without limitation. For example, the thermal, polymerization initiator and the like described above in the polymerization and curing of the polymerizable monomer penetrating the inorganic aggregate particles may be used. In general, photopolymerization is frequently used to cure (polymerize) a dental curable composition, because the operation is simple during its use. For this reason, a photopolymerization initiator is also preferably used as the polymerization initiator in the dental curable composition, of the present invention.

Preferred examples of the photopolymerization initiator include benzoinalkyl ethers, benzyl totals, benzophenones, α-diketones, thioxanthone compounds, and bisacylphosphine oxides. A reducing agent is often added to the photopolymerization initiator. Examples of such a reducing agent include aromatic amines, aliphatic amines, aldehydes, and sulfur-containing compounds. Furthermore, as needed, a trihalomethyltriazine compound, an aryliodonium salt, or the like may also be added. The polymerization initiator is generally added in an amount of 0.01 to 10 parts by mass based on 100 parts by mass of the polymerizable monomer.

Any other inorganic filler may also be added to the dental curable composition, as long as the effects of the present invention are not impaired. As the other inorganic filler, any publically known filler used in a dental application may be used without limitation. For example, the other inorganic filler may be inorganic particles mace of the same material as the above mentioned inorganic primary particles.

Furthermore, any publically known additive may be added to the dental curable composition of the present invention, as long as the effects are not significantly interfered. Examples of such an additive include a polymerization inhibitor, a pigment, an ultraviolet absorbing agent, and a fluorescent agent.

The dental curable composition of the present invention is generally manufactured by a process including sufficiently kneading predetermined amounts of the above mentioned respective essential components and any optional component(s) added as needed to form a paste, and degassing the paste under reduced pressure to remove air bubbles. While the dental, curable composition may be used for any application without limitation, particularly preferred applications include those to dental composite restorative materials such as dental restorative filling materials and indirect dental restorative materials.

EXAMPLES

Hereinafter, the present invention is more specifically described with reference to Examples, which however are not intended to limit the present invention. Listed, below are abbreviations for compounds used, in the Examples and the Comparative Examples below, such as polymerizable monomers, inorganic particles, polymerization initiators, and water absorbing resins.

A) Polymerizable Monomers
3G: Triethylene glycol dimethacrylate
HD: 1,6-hexanediol dimethacrylate
GMA: 2,2-bis[(3-methacryloyloxy-2-hydroxypropyloxy)phenyl]propane
UDMA: 1,6-bis(methacrylethyloxycarbonylamino)-2,2-4-trimethylhexane
D2.6E: Compound represented by the following formula:

[Chemical Formula 1]

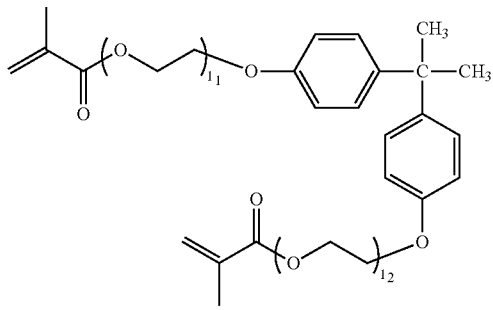

A mixture in which the average $(l_1+l_2)$ is 2.6.

B) Inorganic Particles
F-1: Spherical (an average degree of symmetry of 0.95) primary particles of silica-zirconia with an average particle diameter of 500 nm produced by a sol-gel method
F-2: Spherical (an average degree of symmetry of 0.95) primary particles of silica-zirconia with an average particle diameter of 400 nm produced by a sol-gel method
F-3: Spherical (an average degree of symmetry of 0.95) primary particles of silica-titania wish an average particle diameter of 80 nm produced by a sol-gel method
F-4: Spherical (an average degree of symmetry of 0.95) primary particles of silica-zirconia with an average particle diameter of 700 nm produced by a sol-gel method
F-5: Nearly spherical (an average degree of symmetry of 0.60) primary particles of ytterbium trifluoride with an average particle diameter of 100 nm produced by a sol-gel method.

C) Polymerization Initiators
AIBN: Azobisisobutyronitrile
CQ: Camphorquinone
DMBE: Ethyl N,N-dimethyl-p-benzoate D) Water Absorbing Resins (SAP)
SAP1: sodium, polyacrylate, manufactured by Polysciences, Inc., with a weight-average molecular weight of 6000
SAP2: starch-acrylonitrile graft copolymer obtained by a method described below, with a weight-average molecular weight of 5500
According to a method disclosed in JP 49-43395 B, 9.7 g of amylose (manufactured by Tokyo Chemical Industry Co., Ltd., with a weight-average molecular weight of 2800) were added and dissolved in 133 ml of water under stirring for 30 minutes at 45° C. Subsequently, 9.7 g of acrylonitrile (a molar ratio of starch:acrylonitrile being 1:3) and 7 ml solution of eerie ammonium nitrate were sequentially added in the mixture to react for 1 hour. The mixture was then neutralized to a pH of 6 to 7, and the reaction product was subjected to filtration-washing and vacuum drying until the moisture content reached less than 3%, so that the starch-acrylonitrile graft copolymer was obtained.

SAP3: sodium polyacrylate, manufactured by Polysciences, Inc., with a weight-average molecular weight of 2000
SAP4: sodium polyacrylate, "ARONVIS-SX", manufactured by TOAGOSEI Co., Ltd., with a weight-average molecular weight of 5000000
SAP5: polyethylene glycol, manufactured by Wako Pure Chemical Industries, Ltd., wish a weight-average molecular weight of 2000
SAP6: polyacrylamide, "Accoflock N-100", manufactured by MT AquaPolymer, Inc., with a weight-average molecular weight of 17000000
SAP7: ethyleneglycol, manufactured by Wako Pure Chemical Industries, Ltd., with a molecular weight of 62

The average particle diameter and the average degree of symmetry of inorganic primary particles, the properties (the average particle diameter, the central cross section observation, the average degree of symmetry, the micropore volume, and the average pore diameter) of inorganic aggregate particles and organic-inorganic composite fillers, the content of an organic resin in an organic-inorganic composite filler, the measurement of the bending strength, the evaluation of the transparency, and the evaluation of the discoloration resistance were measured or performed according to methods described below.

(1) Average Particle Diameter and Average Degree of Symmetry of Inorganic Primary Particles Constituting Organic-Inorganic Composite Filler Organic-inorganic composite fillers were photographed at a magnification of 5000 to 100000 times with the use of a scanning electron microscope (a trade name "XL-30S FEG", manufactured by PHILIPS). Using an image analysis software (a trade name "IP-1000PC", manufactured by Asahi Kasei Engineering Corporation), the image was processed, and the circle-equivalent diameter (particle diameter), maximum length, minimum width, and number of primary particles in a unit field of vision were determined. The number of the particles observed was at least 100.

The average volume diameter of primary particles was calculated using the formula below and used as the average particle diameter.

[Mathematical Formula 4]

$$\text{Average particle diameter: } X = \sqrt[3]{\frac{\sum_{i=1}^{n} X_i^3}{n}} \text{ Average volume diameter}$$

n: the number of observed particles
Xi: the particle diameter (diameter) of the i-th particle The number (n) of primary particles, the long diameter (Li) (the maximum length of primary particle), and the minimum width (Bi) (the diameter in the direction perpendicular to the long diameter) observed in a unit field of vision were also determined. The average degree of symmetry of inorganic primary particles was calculated using the formula below.

$$\text{Average degree of symmetry} = \frac{\sum_{i=1}^{n} Bi/Li}{n} \quad \text{[Mathematical Formula 5]}$$

(2) Average Particle Diameter (Particle Size) of Inorganic Aggregate Particles

In 10 ml of ethanol, 0.1 g of inorganic aggregate particles was dispersed and sufficiently shaken by hand. The dispersion was analyzed by a laser diffraction/scattering method with the use of a particle size distribution meter ("LS230", manufactured by Beckman Coulter, Inc.), and the median diameter of the volume statistics was determined using an optical model. "Fraunhofer".

(3) Average Particle Diameter (Particle Size) of Organic-Inorganic Composite Fillers The particle size was determined by the same procedure as in the case of (2) inorganic aggregate particles, except that supersonic wave was applied for 20 minutes in the process of dispersing organic-inorganic composite fillers in ethanol.

(4) Central Cross Section Observation of Organic-Inorganic Composite Fillers (Presence or Absence of Macro Void)

A resin for embedding organic-inorganic composite fillers was prepared by mixing the following polymerizable monomers and polymerization initiators.

55 parts by mass of D2.6E
10 parts by mass of 3G
35 parts by mass of UDMA
0.20 parts by mass of CQ
0.35 parts by mass of DMBE A paste was obtained by mixing 1 g of the above mentioned embedding resin and 0.3 g of an organic-inorganic composite filler. The paste was loaded in a frame mold which had a hole of 2×2×10 mm. When the paste was loaded, she frame mold was placed onto a polyester film so that the paste did not leak from the lower part of the hole. Subsequently, a polyester film was brought into pressure contact with the surface of the paste on the side of the upper surface of the frame mold. Through each of the polyester films, both surfaces of the paste were irradiated with light for 30 seconds with the use of a visible ray irradiator "Power-Light" (a trade name; manufactured by Tokuyama Dental Corporation). After the paste was cured, the cured product was taken out from the mold. The resulting cured product was cut with a diamond knife to form a 2×2 mm surface with the use of an ultramicrotome (manufactured by RMC Co., Ltd.). The cut thickness for each cutting with the diamond knife was set to have a thickness of 200 nm, and the cutting was performed until the total cut thickness was reached to 200 μm.

The cut surface of the cured product was photographed at a magnification of 50 to 200 times with the use of a scanning electron microscope (a trade name "XL-30S FEG", manufactured by PHILIPS). In this image, the cross sections of organic-inorganic composite fillers were photographed. Randomly selected in a unit field of vision were 100 cross sections (central cross sections) of organic-inorganic composite fillers which had the long diameter corresponding to a length in the range of 90 to 110% based on the above mentioned average particle diameter of organic-inorganic composite fillers. Among the 100 central cross sections of organic-inorganic composite fillers selected, the number of central cross sections which had a macro void with a maximum width of at least 1 μm was counted.

(5) Average Degree of Symmetry of Organic-Inorganic Composite Fillers

Organic-inorganic composite fillers were photographed at a magnification of 50 to 200 times with the use of a scanning electron microscope (a trade name "XL-30S FEG", manufactured by PHILIPS). Using an image analysis software (a trade name "IP-1000PC", manufactured by Asahi Kasei Engineering Corporation), the image was processed, and the number (n) of primary particles, the long diameter (Li) (the maximum length of the primary particle), and the minimum width (Hi) (the diameter in the direction perpendicular to the long diameter) observed in a unit field of vision were determined. The number of the organic-inorganic composite fillers observed was at least 100. The average degree of symmetry of the organic-inorganic composite fillers was calculated using the formula below.

$$\text{Average degree of symmetry} = \frac{\sum_{i=1}^{n} Bi/Li}{n} \quad \text{[Mathematical Formula 6]}$$

(6) Volume and Average Pore Diameter of Micropores in Inorganic Aggregate Particles and Organic-Inorganic Composite Fillers A mercury porosimeter (a trade name "PoreMaster", manufactured by Quantachrome) was used. In a measurement cell, 0.2 g of inorganic aggregate particles or organic-inorganic composite fillers was placed and the micropore volume distribution was measured. The volumes within the pore diameter range of 1 to 500 nm in the micropore volume distribution were integrated to determine the micropore volume. Concerning the micropores in this range, the median micropore diameter was also calculated from the micropore volume distribution and used as the average pore diameter of aggregation gaps.

(7) Content of Organic Resin in Organic-Inorganic Composite Filler

The organic resin content was measured by the procedure described below with the use of a thermogravimetry-differential thermal analyzer (a trade name "TG/DT/A 6300", manufactured by SII NanoTechnology Inc.). In an aluminum pan, 0.03 g of an organic-inorganic composite filler as a sample was placed. Heating was performed according to the schedule: a rate of temperature increase of 5° C./minute, an upper limit temperature of 500° C., and an upper limit temperature holding time of 30 minutes, while the mass reduction was measured. Using the resulting mass reduction, the mass ratio of organic resin and inorganic particles was determined, and the amount (parts by mass) of the organic resin based on 100 parts by mass of the inorganic particles was calculated. In the thermogravimetry-differential thermal analysis, 0.03 g of aluminum oxide was used as a reference material.

(8) Method for Measuring Bending Strength

Into an organic matrix containing polymerizable monomers and photopolymerization initiators in amounts according to the formulation described below, an inorganic particle and the organic-inorganic composite filler prepared in each of the Examples and the Comparative Examples in amounts as described below were added. Under red light, the mixture was uniformly kneaded in the mortar, and degassed to prepare a dental curable composition.

55 parts by mass of D2.6E
10 parts by mass of 3G
35 parts by mass of UDMA 0.20 parts by mass of CQ
0.35 parts by mass of DMBE
240 parts by mass of organic-inorganic composite filler
160 parts by mass of F-1

A paste of this dental curable composition was loaded in a stainless steel frame mold with the use of a filling instrument. A polypropylene sheet, was brought into pressure contact, with the surface of the loaded paste, and the paste was irradiated with light through the polypropylene sheet. The irradiation with light was performed with the use of a visible ray irradiator "Powerlight" (a trade name; manufactured by Tokuyama Dental Corporation). The irradiation window of the visible ray irradiator was brought into close contact with the polypropylene sheet, and one side surface was irradiated with light three times for 30 seconds each from different locations in such a manner that the curable composition was entirely irradiated with light. Subsequently, the opposite side surface was also irradiated with light in the same manner three times for 30 seconds each. According to these steps, the paste was polymerized so that a cured product was obtained.

The cured product was shaped into a rectangular prism of 2×2×25 mm with the use of waterproof abrasive paper #800. The resulting sample piece was mounted on a tester (a trade name "Autograph AG5000D", manufactured by Shimadzu Corporation) and measured for three-point bending fracture strength under the testing conditions of a support distance of 20 mm and a cross-head speed of 1 mm/minute. Five test pieces were evaluated, and the average value was used as the bending strength.

(9) Evaluation of Transparency

A paste of the same dental curable composition as the paste prepared by the above mentioned method (8) was loaded in a mold having a through hole with 7 mm diameter φ×1 mm depth. Polyester films were brought into pressure contact with the surfaces of the paste at both ends of the hole. Through each of the polyester films, both surfaces of the paste were irradiated with light for 30 seconds with the use of a visible ray irradiator (Powerlight, manufactured by Tokuyama Dental Corporation). After the paste was cared, the cured product was taken out from the mold. The tristimulus Y value of the cured product (background color being black and white) was measured with the use of a color difference meter (a trade name "TC-1800MK-II", manufactured by Tokyo Denshoku Co., Ltd.). The contrast ratio was calculated based on the following formula and used as an indicator of the transparency.

CONTRAST RATIO=($Y$ VALUE IN CASE OF SLACK BACKGROUND)/($Y$ VALUE IN CASE OF WHITE BACKGROUND)

(10) Evaluation of Discoloration Resistance

A paste of the same dental curable composition as the paste prepared by the above mentioned method (8) was loaded in a frame mold having a punched groove with 10 mm length×10 mm width×2 mm height. Polyester films were brought into pressure contact with the surfaces of the paste at both ends of the groove. Through each of the polyester films, both surfaces of the paste were irradiated with light for 30 seconds with the use of a visible ray irradiator "Powerlight" (a trade name, manufactured by Tokuyama Dental Corporation). After the paste was cured, the cured product was taken out from the mold. The surface of the cured product was polished with waterproof abrasive paper #1500. The surface thereof was then subjected to finish polishing for 1 minute with the use of "Soflex-Superfine" (a trade name; manufactured by 3M Company).

The L*, a*, and b* of the cured and polished product before coloration were measured with the use of a color difference meter (a trade name "TC-1800MK-II", manufactured by Tokyo Denshoku Co., Ltd.). Subsequently, the cured product was immersed in 100 ml aqueous solution containing 5.0% by mass of coffee at 40° C. for 24 hours. After the immersion, the cured product was washed with water and dried, and then the L*, a*, and b* were measured with the color difference meter again. The differences ΔL*, Δa*, and Δb* between the L*, a*, and b* before and after the coloration were calculated, and used in the formula below to determine the colored level (ΔE*).

The aqueous solution containing 5.0% by mass of coffee was prepared by placing 5 g of a coffee powder "NESCAFE Excella" (manufactured by Nestle Ltd.) and 95 g of water in a beaker, and stirring the mixture with a magnetic stirrer for one hour.

$$\Delta E^* = (\Delta L^{*2} + \Delta a^{*2} + \Delta b^{*2})^{1/2}$$

Example 1

One hundred g of inorganic particles F-1 and 0.4 g of water absorbing resin SAP1 were added to 200 g of water, and an aqueous dispersion thereof was obtained with the use of a circulating pulverizer "SC Mill" (a trade name; manufactured by Mitsui Mining Company, Ltd.).

On the other hand, 4 g (0.016 mol) of γ-methacryloyloxypropyltrimethoxysilane and 0.003 g or acetic acid were added to 80 g of water, and the mixture was stirred for 1 hour and 30 minutes, so that a uniform solution with a pH of 4 was obtained. The solution was added to the above mentioned inorganic particle dispersion and mixed uniformly. Thereafter, the dispersion was granulated by a spray drying method, including supplying while lightly stirring the dispersion onto a disk rotating at high speed.

A spray drier having a rotary disk for atomization by centrifugal force (Spray Drier "TSR-2W", a trade name; manufactured by Sakamoto Giken K.K.) was used to perform the spray drying. The rotational speed of the disk was 10000 rpm, and the temperature of the air in the drying atmosphere was 200° C. Subsequently, a powder produced by the granulation procedure using the spray drying was vacuum-dried at 60° C. for 18 hours, so that 71 g of spherical inorganic aggregate particles were obtained.

The aggregation gaps in the inorganic aggregate particles had a micropore volume of 0.24 cm³/g, and an average pore diameter of 48 nm. In addition, the inorganic aggregate particles had an average particle diameter of 35.3 μm.

Subsequently, 0.625 g of D2.65 and 1,155 g of 3G as the polymerizable monomer, 0,005 g of AIBN as the polymerization initiator, and 5.0 g of methanol as an organic solvent were mixed to form a polymerizable monomer solution (containing 35.6 parts by mass of the polymerizable monomer based on 100 parts by mass of the organic solvent), and then 10.0 g of the above mentioned inorganic aggregate particles was immersed in the polymerizable monomer solution. The mixture was sufficiently stirred until it was confirmed that the mixture was turned into a slurry, and then allowed to stand for 1 hour.

The above mentioned mixture was transferred into a rotary evaporator. While stirred, the mixture was dried for 1 hour under the conditions of a reduced pressure of 10 hue and a heating temperature of 10° C. (with the use of a hot water bath), so that the organic solvent was removed. After the removal of the organic solvent, a highly-fluid powder was obtained. The cohesiveness of this powder was not found.

While stirred in the rotary evaporator, the resulting powder was heated for 1 hour under the conditions of a reduced pressure of 10 hPa and a heating temperature of 100° C. (with the use of an oil bath), so that the polymerizable monomer in the powder was polymerized and cured. According to these steps, 8.5 g of a spherical organic-inorganic composite filler was obtained.

The aggregation gaps in the organic-inorganic composite filler had a micropore volume of 0.08 cm$^3$/g, and an average pore diameter of 27 nm. The organic-inorganic composite fillers had an average particle diameter of 36.0 μm and an average degree of symmetry of 0.85, and it was also confirmed that the inorganic primary particles of the fillers had an average particle diameter of 200 nm. The measured organic resin content in the organic-inorganic composite filler was 17.8 parts by mass based on 100 parts by mass of inorganic particles F-1. Based on the observation of the central cross sections of the organic-inorganic composite fillers, a macro void was observed in 4 out of 100 organic-inorganic composite fillers.

Example 2

Using the same process as in Example 1, except that 0.4 g of SAP2 was used as the water absorbing resin, 66 g of inorganic aggregate particles were obtained. The aggregation gaps in the inorganic aggregate particles had a micropore volume of 0.24 cm$^3$/g, and an average pore diameter of 48 nm. In addition, the inorganic aggregate particles had an average particle diameter of 35.6 μm.

Subsequently, 8.1 g of an organic-inorganic composite filler was obtained using the inorganic aggregate particles by the same process as in Example 1. The aggregation gaps in the organic-inorganic composite filler had a micropore volume of 0.08 cm$^3$/g, and an average pore diameter of 28 nm. The inorganic aggregate particles had an average particle diameter of 36.5 μm, and an average degree of symmetry of 0.85. It was also confirmed that the inorganic primary particles of the inorganic aggregate particles had an average particle diameter of 200 nm.

The measured organic resin content in the organic-inorganic composite filler was 17.8 parts by mass based on 100 parts by mass of inorganic particles F-1. Based on the observation of the central cross sections of the organic-inorganic composite fillers, a macro void was observed in 3 out of 100 organic-inorganic composite fillers.

Examples 3 to 13

The same process as in Example 1 was used, except that the type of the inorganic particles, and the amount of the water absorbing resin used in the production of the inorganic aggregate particles, as well as the type and amount of the polymerizable monomer and the polymerization initiator contained in the polymerizable monomer solution were each changed as shown in Table 1. As a result, spherical organic-inorganic composite fillers were obtained in either process. The physical properties of each resulting organic-inorganic composite filter were measured as in Example 1. The results are shown in Table 2, Comparative Example 1

30 g of the same inorganic aggregate particles as in Example 1, 3,465 g of D2.6E and 6.435 g of 3G as the polymerizable monomers and 0.03 g of AIBN as the polymerization initiator were each placed in a mortar and mixed together to prepare a paste-like mixture. The paste-like mixture was degassed under reduced pressure and then subjected to polymerization and curing at 100° C. for 30 minutes. The cured product was ground in a vibratory ball mill (zirconia ball diameter: 5 mm), and the ground product was sieved, so that particles with a diameter of at least 100 μm were removed.

The resulting irregular form organic-inorganic composite fillers had an average particle diameter of 20.3 μm. A micropore was not confirmed by the measurement with a mercury porosimeter. The measured organic resin content in the organic-inorganic composite filler was 33.0 parts by mass based on 100 parts by mass of inorganic particles F-1. In addition, based on the observation of the central cross sections of the organic-inorganic composite fillers, a macro void was observed in 1 out of 1.00 organic-inorganic composite fillers.

In case of Comparative Example 1, the solvent was not made to coexist during the immersion with the polymerizable monomer. As a result, the inside of the inorganic aggregate particles was not sufficiently impregnated with the polymerizable monomer, it is therefore considered that the polymerisable monomer was distributed near the surface of the inorganic aggregate particles to close the micropores.

Comparative Example 2

Using the same process as in Example 1, except that the water absorbing resin was not added, a slurry was prepared and the spray drying was performed, so that mixed organic-inorganic composite fillers with a spherical, dimpled or toroidal shape were produced. The physical properties of the resulting organic-inorganic composite filler were measured as in Example 1. The results are shown in Table 2.

In case of Comparative Example 2, the water absorbing resin was not used, it is therefore considered that drastic drying occurred during the spray drying so that the organic-inorganic composite fillers had many macro voids.

Comparative Example 3

Using the same process as in Example 1, except that a water absorbing low molecular weighs compound was used instead of the water absorbing resin, an organic-inorganic composite filler was produced. The physical properties of the resulting organic-inorganic composite filler were measured as in Example 1. The results are shown in Table 2.

Examples 14 to 26 and Comparative Examples 4 to 6

A dental curable composition was prepared using each organic-inorganic composite filler as shown in Table 2, and the measurement of the bending strength, the evaluation of the transparency, and the evaluation of the discoloration resistance were performed. The results are shown together in Table 3.

In Comparative Example 6 was used the organic-inorganic composite filler from Comparative Example 3 in which the water absorbing low molecular weight compound was used. When the water-absorbing low molecular weight compound was used, the absorbed water cannot be completely removed by spray drying and vacuum drying, it is therefore considered that the absorbed water remained in the organic-inorganic composite filler so that the property (bending strength) of the cured product was significantly reduced.

TABLE 1

| | AQUEOUS SUSPENSION | | | | INORGANIC AGGREGATE PARTICLES | | |
|---|---|---|---|---|---|---|---|
| | INORGANIC PARTICLES/ PARTS BY MASS | SAP/PARTS BY MASS | SOLVENT | INORGANIC PARTICLE CONCENTRATION (% BY MASS) | MICROPORE VOLUME ($cm^3/g$) | AVERAGE PORE DIAMETER (nm) | AVERAGE PARTICLE DIAMETER ($\mu m$) |
| EXAMPLE 1 | F-1/100 | SAP1/0.4 | WATER | 33 | 0.24 | 48 | 35.3 |
| EXAMPLE 2 | F-1/100 | SAP2/0.4 | WATER | 33 | 0.24 | 48 | 35.6 |
| EXAMPLE 3 | F-1/100 | SAP1/3 | WATER | 33 | 0.21 | 42 | 35.0 |
| EXAMPLE 4 | F-2/70 F-3/30 | SAP1/0.012 | WATER | 33 | 0.17 | 35 | 32.5 |
| EXAMPLE 5 | F-4/100 | SAP1/10 | WATER | 33 | 0.25 | 208 | 38.3 |
| EXAMPLE 6 | F-4/100 | SAP1/0.4 | WATER | 33 | 0.32 | 245 | 37.2 |
| EXAMPLE 7 | F-1/100 | SAP1/3 | WATER | 10 | 0.26 | 43 | 37.3 |
| EXAMPLE 8 | F-5/100 | SAP1/2 | WATER | 33 | 0.29 | 63 | 34.7 |
| EXAMPLE 9 | F-1/60 F-5/40 | SAP1/0.8 | WATER | 33 | 0.22 | 51 | 35.5 |
| EXAMPLE 10 | F-1/100 | SAP3/0.4 | WATER | 33 | 0.21 | 43 | 34.2 |
| EXAMPLE 11 | F-1/100 | SAP4/0.4 | WATER | 33 | 0.25 | 48 | 43.0 |
| EXAMPLE 12 | F-1/100 | SAP5/0.4 | WATER | 33 | 0.20 | 41 | 34.9 |
| EXAMPLE 13 | F-1/100 | SAP6/0.4 | WATER | 33 | 0.26 | 52 | 49.2 |
| COMPARATIVE EXAMPLE 1 | F-1/100 | SAP1/0.4 | WATER | 33 | 0.24 | 48 | 35.3 |
| COMPARATIVE EXAMPLE 2 | F-1/100 | —/0 | WATER | 33 | 0.25 | 50 | 40.0 |
| COMPARATIVE EXAMPLE 3 | F-1/100 | SAP7/0.4 | WATER | 33 | 0.17 | 31 | 34.8 |

| | FORMULATION OF POLYMERIZABLE MONOMER SOLUTION | | | | |
|---|---|---|---|---|---|
| | POLYMERIZABLE MONOMER SOLUTION COMPOSITION | | | | PARTS BY MASS OF POLYMERIZABLE MONOMER SOLUTION BASED ON 100 PARTS BY MASS OF INORGANIC AGGREGATE PARTICLES |
| | ORGANIC SOLVENT/PARTS BY MASS | POLYMERIZABLE MONOMER/PARTS BY MASS | POLYMERIZATION INITIATOR/PARTS BY MASS | PARTS BY MASS OF POLYMERIZABLE MONOMER BASED ON 100 PARTS BY MASS OF ORGANIC SOLVENT | |
| EXAMPLE 1 | METHANOL/100 | D2.6E/12.5 3G/23.1 | AIBN/0.10 | 35.6 | 67.9 |
| EXAMPLE 2 | METHANOL/100 | D2.6E/12.5 3G/23.1 | AIBN/0.10 | 35.6 | 67.9 |
| EXAMPLE 3 | METHANOL/100 | D2.6E/12.5 3G/23.1 | AIBN/0.10 | 35.6 | 67.9 |
| EXAMPLE 4 | METHANOL/100 | D2.6E/12.5 3G/23.1 | AIBN/0.10 | 35.6 | 67.9 |
| EXAMPLE 5 | METHANOL/100 | D2.6E/6.25 3G/11.55 | AIBN/0.5 | 17.8 | 67.9 |
| EXAMPLE 6 | METHANOL/100 | GMA/2.8 3G/2.0 HD/3.2 | AIBN/0.02 | 8.0 | 54.0 |
| EXAMPLE 7 | METHANOL/100 | D2.6E/12.5 3G/23.1 | AIBN/0.10 | 35.6 | 67.9 |
| EXAMPLE 8 | METHANOL/100 | D2.6E/12.5 3G/23.1 | AIBN/0.10 | 35.6 | 67.9 |
| EXAMPLE 9 | METHANOL/100 | D2.6E/12.5 3G/23.1 | AIBN/0.10 | 35.6 | 67.9 |
| EXAMPLE 10 | METHANOL/100 | D2.6E/12.5 3G/23.1 | AIBN/0.10 | 35.6 | 67.9 |
| EXAMPLE 11 | METHANOL/100 | D2.6E/12.5 3G/23.1 | AIBN/0.10 | 35.6 | 67.9 |
| EXAMPLE 12 | METHANOL/100 | D2.6E/12.5 3G/23.1 | AIBN/0.10 | 35.6 | 67.9 |
| EXAMPLE 13 | METHANOL/100 | D2.6E/12.5 3G/23.1 | AIBN/0.10 | 35.6 | 67.9 |
| COMPARATIVE EXAMPLE 1 | — | D2.6E/12.5 3G/23.1 | AIBN/0.10 | — | — |
| COMPARATIVE EXAMPLE 2 | METHANOL/100 | D2.6E/12.5 3G/23.1 | AIBN/0.10 | 35.6 | 67.9 |
| COMPARATIVE EXAMPLE 3 | METHANOL/100 | D2.6E/12.5 3G/23.1 | AIBN/0.10 | 35.6 | 67.9 |

TABLE 3

RELATING TO ORGANIC-INORGANIC COMPOSITE FILLERS

| | MICROPORE VOLUME (cm³/g) | AVERAGE PORE DIAMETER (nm) | PARTS BY MASS OF AMOUNT OF ORGANIC RESIN BASED ON 100 PARTS BY MASS OF INORGANIC PARTICLES | AVERAGE PARTICLE DIAMETER (μm) | AVERAGE DEGREE OF SYMMETRY | NUMBER OF ORGANIC-INORGANIC COMPOSITE FILLERS HAVING MACRO VOID OUT OF 100 ORGANIC-INORGANIC COMPOSITE FILLERS |
|---|---|---|---|---|---|---|
| EXAMPLE 1 | 0.08 | 27 | 17.8 | 36.0 | 0.85 | 4 |
| EXAMPLE 2 | 0.08 | 28 | 17.8 | 36.5 | 0.85 | 3 |
| EXAMPLE 3 | 0.06 | 20 | 20.6 | 35.5 | 0.90 | 1 |
| EXAMPLE 4 | 0.04 | 14 | 17.4 | 32.8 | 0.80 | 7 |
| EXAMPLE 5 | 0.16 | 172 | 18.7 | 39.0 | 0.95 | 0 |
| EXAMPLE 6 | 0.27 | 230 | 4.5 | 37.5 | 0.85 | 3 |
| EXAMPLE 7 | 0.07 | 24 | 20.4 | 37.7 | 0.80 | 6 |
| EXAMPLE 8 | 0.12 | 40 | 19.0 | 35.2 | 0.90 | 2 |
| EXAMPLE 9 | 0.06 | 27 | 18.3 | 36.4 | 0.85 | 5 |
| EXAMPLE 10 | 0.04 | 21 | 18.4 | 35.3 | 0.90 | 2 |
| EXAMPLE 11 | 0.09 | 28 | 17.6 | 44.2 | 0.85 | 3 |
| EXAMPLE 12 | 0.03 | 18 | 18.6 | 35.5 | 0.90 | 1 |
| EXAMPLE 13 | 0.10 | 32 | 17.6 | 50.0 | 0.85 | 4 |
| COMPARATIVE EXAMPLE 1 | 0.00 | 0 | 33.0 | 27.5 | — | 1 |
| COMPARATIVE EXAMPLE 2 | 0.09 | 30 | 17.4 | 40.4 | 0.50 | 83 |
| COMPARATIVE EXAMPLE 3 | 0.02 | 14 | 20.5 | 36.3 | 0.90 | 0 |

TABLE 4

| | ORGANIC-INORGANIC COMPOSITE FILLER | BENDING STRENGTH (MPa) | TRANSPARENCY (Yb/Yw) | DISCOLORATION RESITANCE (ΔE*) |
|---|---|---|---|---|
| EXAMPLE 14 | FILLER FROM EXAMPLE 1 | 141 | 0.42 | 7.2 |
| EXAMPLE 15 | FILLER FROM EXAMPLE 2 | 121 | 0.41 | 7.3 |
| EXAMPLE 16 | FILLER FROM EXAMPLE 3 | 130 | 0.42 | 7.5 |
| EXAMPLE 17 | FILLER FROM EXAMPLE 4 | 145 | 0.44 | 7.3 |
| EXAMPLE 18 | FILLER FROM EXAMPLE 5 | 118 | 0.45 | 7.9 |
| EXAMPLE 19 | FILLER FROM EXAMPLE 6 | 135 | 0.39 | 7.1 |
| EXAMPLE 20 | FILLER FROM EXAMPLE 7 | 129 | 0.42 | 7.9 |
| EXAMPLE 21 | FILLER FROM EXAMPLE 8 | 126 | 0.49 | 7.8 |
| EXAMPLE 22 | FILLER FROM EXAMPLE 9 | 138 | 0.47 | 7.5 |
| EXAMPLE 23 | FILLER FROM EXAMPLE 10 | 125 | 0.44 | 8.0 |
| EXAMPLE 24 | FILLER FROM EXAMPLE 11 | 131 | 0.42 | 7.4 |
| EXAMPLE 25 | FILLER FROM EXAMPLE 12 | 117 | 0.45 | 8.1 |
| EXAMPLE 26 | FILLER FROM EXAMPLE 13 | 127 | 0.42 | 7.1 |
| COMPARATIVE EXAMPLE 4 | FILLER FROM COMPARATIVE EXAMPLE 1 | 88 | 0.41 | 7.3 |
| COMPARATIVE EXAMPLE 5 | FILLER FROM COMPARATIVE EXAMPLE 2 | 143 | 0.41 | 15.2 |
| COMPARATIVE EXAMPLE 6 | FILLER FROM COMPARATIVE EXAMPLE 3 | 90 | 0.49 | 8.5 |

The invention claimed is:

1. An organic-inorganic composite filler for dental materials in the form of a powder, having an average composite particle diameter of 3 to 100 μm, comprising:

inorganic aggregate particles formed by aggregation of inorganic primary particles with an average particle diameter of 10 to 1000 nm;

an organic resin phase including a cured polymer of a polymerizable monomer covering surfaces of the inorganic primary particles and bonding the inorganic primary particles to each other, and 0.01 to 10 parts by mass of a water absorbing resin based on 100 parts by mass of the inorganic aggregate particles, wherein the water absorbing resin is selected from the group consisting of a polysaccharide based water absorbing resin, a polyvinyl alcohol based water absorbing resin, an acrylate based water absorbing resin, an acrylamide based water absorbing resin and a polyether based compound; and aggregation gaps with a volume of micropores formed between parts of the organic resin phase of 0.01 to 0.30 cm³/g in pore volume measurement within a pore diameter range of 1 to 500 nm, as measured by a mercury intrusion technique, wherein in a cross section passing through centers of the inorganic aggregate particles, based on 100 measured inorganic particles, there are 10 or less inorganic aggregate particles having a macro void with a maximum width of at least 1 μm.

2. The organic-inorganic composite filler according to claim 1, wherein average degree of symmetry is at least 0.6.

3. The organic-inorganic composite filler according to claim 1, wherein average particle diameter of the inorganic aggregate particles is from 3 to 100 μm.

4. The organic-inorganic composite filler according to claim 1, wherein the water absorbing resin is an acrylate based water absorbing resin with a weight-average molecular weight of 2000 to 20000000 g/mol.

5. The organic-inorganic composite filler according to claim 1, wherein the cured polymer of the polymerizable monomer included in the organic resin phase is a cured polymer of a (meth)acrylic polymerizable monomer.

6. The organic-inorganic composite filler according to claim 1, wherein content of the cured polymer of the polymerizable monomer in the organic resin phase is, based on 100 parts by mass of the inorganic primary particles, from 1 to 40 parts by mass.

7. The organic-inorganic composite filler according to claim 1, wherein the inorganic primary particles are silica-based complex oxide particles.

8. A method for producing the organic-inorganic composite filler according to claim 1, comprising the steps of:
spray drying an aqueous suspension of the inorganic primary particles with an average particle diameter of 10 to 1000 nm containing the water absorbing resin to granulate the inorganic primary particles, so that the inorganic aggregate particles are formed in which the surfaces of the inorganic primary particles are attached with the water absorbing resin;
immersing the formed inorganic aggregate particles with a polymerizable monomer solution containing 100 parts by mass of an organic solvent, 3 to 70 parts by mass of the polymerizable monomer, and an effective amount of a polymerization initiator;
removing the organic solvent from the immersed inorganic aggregate particles; and
polymerizing and curing the polymerizable monomer with which the inorganic aggregate particles are impregnated.

9. The method for producing the organic-inorganic composite filler according to claim 8, wherein the inorganic aggregate particles are inorganic aggregate particles with a volume of micropores of 0.015 to 0.35 $cm^3/g$ as measured by a mercury intrusion technique, wherein each of the micropores corresponds to a pore with a pore diameter in the range of 1 to 500 nm.

10. A dental curable composition, comprising: the organic-inorganic composite filler according to claim 1; a polymerizable monomer; and a polymerization initiator.

11. The organic-inorganic composite filler according to claim 1, wherein the content of the water absorbing resin relative to the cured polymer of the polymerizable monomer is, based on 100 parts by mass of the cured polymer of the polymerizable monomer, from 0.05 to 50 parts by mass.

12. The organic-inorganic composite filler according to claim 1, wherein
the polysaccharide based water absorbing resin is hyaluronic acid, a starch based water absorbing resin, or a cellulose based water absorbing resin;
the polyvinyl alcohol based water absorbing resin is polyvinyl alcohol or ethylene-vinyl alcohol copolymer;
the acrylate based water absorbing resin is sodium polyacrylate or sodium salt of acrylic acid-vinyl alcohol copolymer;
the acrylamide based water absorbing resin is polyacrylamide or N-substituted acrylamide; and
the polyether based compounds is polyethylene glycol or polyethylene oxide.

13. The organic-inorganic composite filler according to claim 12, wherein
the starch based water absorbing resin is starch-acrylonitrile graft copolymer, starch-acrylic acid graft copolymer, or starch-acrylate salt graft copolymer; and
the cellulose based water absorbing resin is cellulose-acrylonitrile graft copolymer or carboxymethyl cellulose.

* * * * *